(12) United States Patent
Felder et al.

(10) Patent No.: US 9,597,074 B2
(45) Date of Patent: Mar. 21, 2017

(54) ENDOLUMINAL STAPLER WITH ROTATING WHEEL CAM FOR MULTI-STAPLE FIRING

(71) Applicant: Ethicon Endo-Surgery, Inc., Cincinnati, OH (US)

(72) Inventors: Kevin D. Felder, Loveland, OH (US); Jason L. Harris, Hamilton, OH (US); Rudolph H. Nobis, Mason, OH (US); Lawrence Crainich, Charlestown, NH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 773 days.

(21) Appl. No.: 13/968,040

(22) Filed: Aug. 15, 2013

(65) Prior Publication Data
US 2015/0048141 A1     Feb. 19, 2015

(51) Int. Cl.
*A61B 17/04*     (2006.01)
*A61B 17/10*     (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ............ A61B 17/07207; A61B 17/068; A61B 2017/07278; A61B 17/072;
(Continued)

(56) References Cited

U.S. PATENT DOCUMENTS 6,488,196 B1    12/2002  Fenton, Jr.
7,278,563 B1 *  10/2007  Green ............... A61B 17/07207
                                              227/176.1
(Continued)

FOREIGN PATENT DOCUMENTS

EP        2374419 A2      10/2011
WO    WO 2012/166521      12/2012

OTHER PUBLICATIONS

International Search Report and Written Opinion dated Jan. 12, 2015 for Application No. PCT/US2014/050487.
Non-Provisional U.S. Appl. No. 13/780,379, filed Feb. 28, 2013.

*Primary Examiner* — Robert Long
(74) *Attorney, Agent, or Firm* — Frost Brown Todd LLC

(57) ABSTRACT

A surgical stapler has a body, a shaft assembly extending distally from the body, and an end effector coupled with a distal end of the shaft assembly. The end effector has a stapling head assembly, an anvil, and a vacuum port. The vacuum port is operable to draw tissue between the stapling head assembly and the anvil. The anvil is operable to move toward and away from the stapling head assembly to thereby capture the tissue drawn between the stapling head assembly and the anvil. The stapling head assembly comprises a plurality of wheel assemblies and staple cartridges. At least one wheel assembly is operable to rotate to thereby move the anvil toward and away from the body. The remaining wheel assemblies are operable to rotate to thereby drive staples through the captured tissue. The body includes user input features operable to drive the wheel assemblies.

19 Claims, 43 Drawing Sheets

(51) Int. Cl.
*A61B 17/068* (2006.01)
*A61B 17/11* (2006.01)
*A61B 17/072* (2006.01)
*A61B 17/00* (2006.01)
*A61B 17/29* (2006.01)
*A61B 17/30* (2006.01)

(52) U.S. Cl.
CPC ..... *A61B 17/11* (2013.01); *A61B 2017/00314* (2013.01); *A61B 2017/00323* (2013.01); *A61B 2017/00818* (2013.01); *A61B 2017/07271* (2013.01); *A61B 2017/07278* (2013.01); *A61B 2017/1107* (2013.01); *A61B 2017/2927* (2013.01); *A61B 2017/2936* (2013.01); *A61B 2017/2944* (2013.01); *A61B 2017/306* (2013.01)

(58) Field of Classification Search
CPC  A61B 2017/00473; A61B 2017/07214; A61B 2017/2903; A61B 2017/00323; A61B 2017/2926; A61B 17/11; A61B 2017/00561
USPC ............................. 227/175.1–182.1; 606/219
See application file for complete search history.

(56) References Cited

U.S. PATENT DOCUMENTS

| | | |
|---|---|---|
| 8,517,242 B2 | 8/2013 | Marczyk et al. |
| 2006/0016846 A1* | 1/2006 | Joyce ................... B25C 5/0242 227/132 |
| 2008/0149684 A1* | 6/2008 | Viola ................ A61B 17/07207 227/176.1 |
| 2011/0248064 A1* | 10/2011 | Marczyk .......... A61B 17/07207 227/114 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0168485 A1* | 7/2012 | Marczyk ............. A61B 17/072 227/176.1 |
| 2013/0023868 A1 | 1/2013 | Worrell et al. |
| 2013/0153626 A1* | 6/2013 | Felder ................. A61B 17/072 227/175.1 |
| 2013/0153642 A1* | 6/2013 | Felder ................. A61B 17/072 227/181.1 |

* cited by examiner

ENDOLUMINAL STAPLER WITH ROTATING WHEEL CAM FOR MULTI-STAPLE FIRING

BACKGROUND

Metabolic disease may result in various conditions including obesity, hypertension, diabetes, coronary artery disease, stroke, congestive heart failure, multiple orthopedic problems, pulmonary insufficiency, sleep apnea, infertility, and markedly decreased life expectancy. Additionally, the complications or co-morbidities associated with metabolic disease may affect an individual's quality of life. Accordingly, the monetary, physical, and psychological costs associated with metabolic disease may be substantial in some cases.

A variety of bariatric surgical procedures have been developed to treat complications of metabolic disease, such as obesity. One such procedure is the Roux-en-Y gastric bypass (RYGB). In a RYGB procedure, a small stomach pouch is separated from the remainder of the gastric cavity and attached to a re-sectioned portion of the small intestine. However, because this complex procedure may require a great deal of operative time, as well as extended and painful post-operative recovery, the RYGB procedure is generally only utilized to treat people with morbid obesity.

In view of the highly invasive nature of the RYGB procedure, other less invasive bariatric procedures have been developed such as the Fobi pouch, bilio-pancreatic diversion, gastroplasty ("stomach stapling"), vertical sleeve gastrectomy, and gastric banding. In addition, implantable devices are known which limit the passage of food through the stomach. Gastric banding procedures, for example, involve the placement of a small band around the stomach near the junction of the stomach and the esophagus to restrict the passage from one part of the digestive tract to another, thereby affecting a patient's feeling of satiety.

While the above-described bariatric procedures may be used for the treatment of morbid obesity, in some cases the risks of these procedures may outweigh the potential benefits for the growing segment of the population that is considered overweight. The additional weight carried around by these persons may still result in significant health complications, but does not necessarily justify more invasive treatment options. However, because conservative treatment with diet and exercise alone may be ineffective for reducing excess body weight in some cases, there is a need for treatment options that are less invasive and lower cost than the procedures discussed above.

It is known to create cavity wall plications through both laparoscopic and endoscopic procedures. Laparoscopic plication techniques can be complicated and complex, however, as one or more surgical entry ports may need to be employed to gain access to the surgical site. Furthermore, laparoscopically approaching the stomach may require separating the surrounding omentum prior to plication formation. In endoscopic procedures, plication depth may suffer due to the size restrictions of the endoscopic lumen. For example, the rigid length and diameter of a surgical device are limited based on what sizes can be reliably and safely passed trans-orally into the stomach. Furthermore, access and visibility within the gastric and peritoneal cavities may be progressively limited in an endoscopic procedure as the extent of the reduction increases, because the volume of the gastric cavity is reduced.

In addition, existing devices for forming endoluminal plications may utilize opposing jaws and a grasper element to draw tissue between the jaws. These devices may approach the cavity wall such that a longitudinal axis of the device is perpendicular to the cavity wall. The grasper element can then be advanced from the center of the open jaws, and used to draw tissue between the jaws to create the fold. However, the geometry of these devices limits the size of the plication that can be formed to approximately the length of the jaws, as the grasper may be able to only draw the cavity wall tissue to the center of the jaws and no further. Moreover, in order to secure a plication with a plurality of fasteners, these devices may need to release the tissue and be repositioned anew to apply each fastener. A merely exemplary plication device is disclosed in U.S. Pat. Pub. No. 2013/0153642, entitled "Devices and Methods for Endoluminal Plication," published Jun. 20, 2013, now U.S. Pat. No. 9,119,615, issued Sep. 1, 2015, the disclosure which is incorporated by reference herein.

While various kinds of bariatric surgical instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
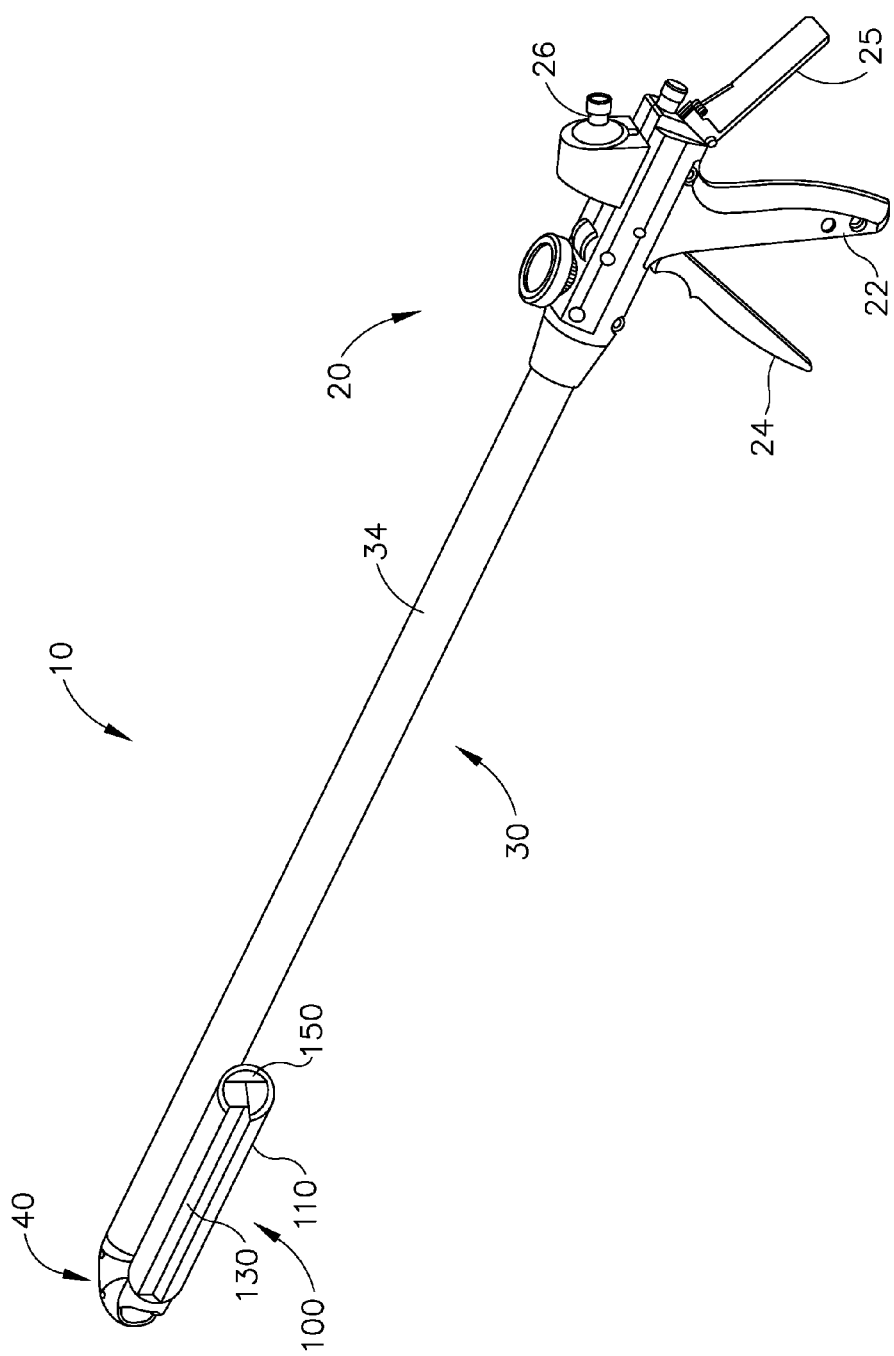
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Endoluminal Stapler

FIGS. 1-5 depict an exemplary endoluminal stapling instrument (10) having a handle assembly (20), a shaft assembly (30), and an end effector (100); each of which will be described in more detail below. Shaft assembly (30) extends distally from handle assembly (20) and end effector (100) is coupled to a distal end of shaft assembly (30). Shaft assembly (30) and end effector (100) are dimensioned to enable shaft assembly (30) and end effector (100) to be inserted transorally through a patient's esophagus, to selectively position end effector (100) in the patient's stomach in a minimally invasive manner. In brief, handle assembly (20) is operable to actuate an anvil (150), a vacuum head (130), and a plurality of stapling assemblies (200) to suction and grasp tissue in the stomach, and to substantially simultaneously drive a plurality of staples (172) through the folded tissue. Staples (172) are bent to form completed staples by anvil (150), which is slidably attached to end effector (100). Accordingly, tissue (2) may be stapled utilizing instrument (10) as shown in FIGS. 20A-22.

A. Exemplary Handle Assembly and Shaft Assembly

Figure 2:
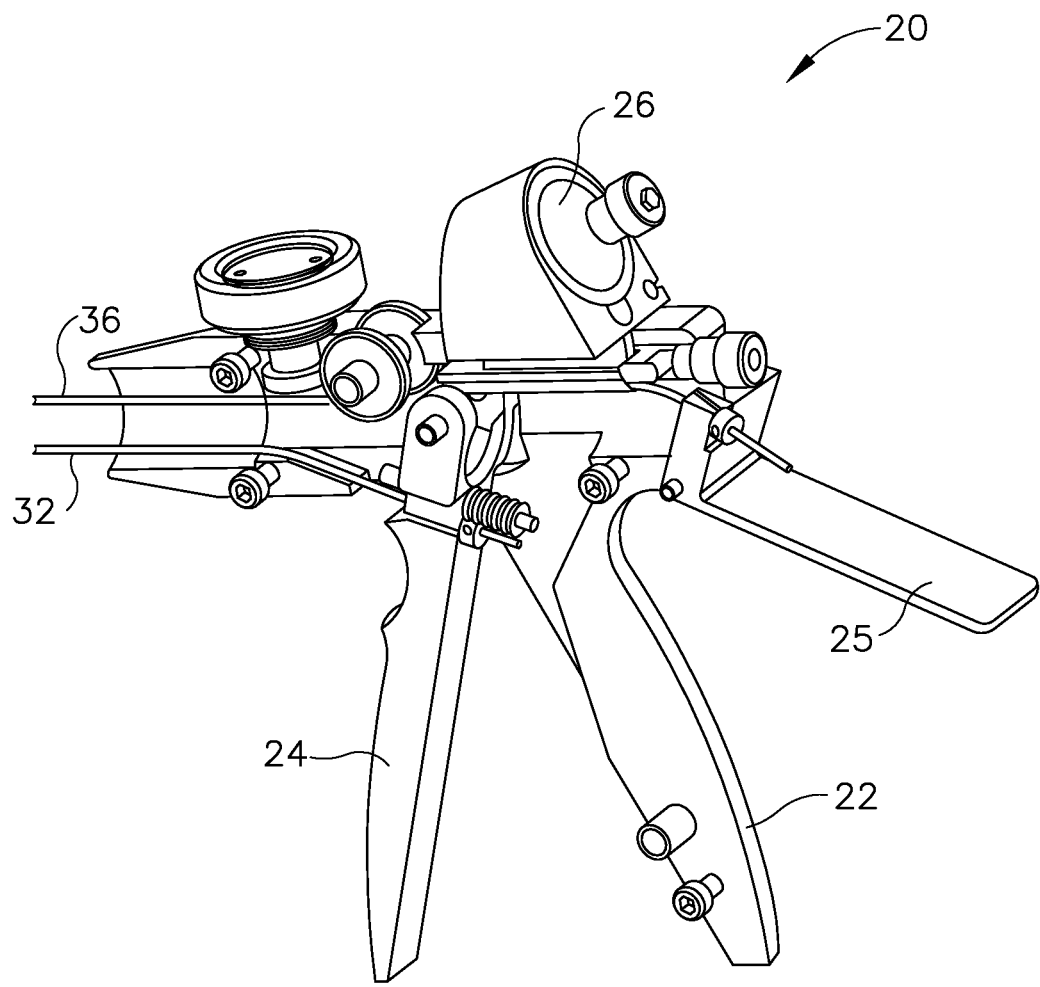
FIG. 2 depicts a perspective view of a handle assembly of the instrument of FIG. 1.

As shown in FIGS. 1-2, handle assembly (20) of the present example includes a pistol grip (22), a pivoting trigger (24), a palm trigger (25), and an articulation control knob (26). While handle assembly (20) of the present example includes manually actuated triggers (24, 25) and knob (26), it should be understood that handle assembly (20) may include various other kinds of user input features in addition to or in lieu of manually actuated triggers (24, 25) and knob (26). Similarly, it should be understood that handle assembly (20) may include one or more motors that are operable to drive end effector (100) and/or other features of instrument (10). Various suitable ways in which instrument (10) may be at least partially motorized will be apparent to those of ordinary skill in the art in view of the teachings herein.

Figure 3:
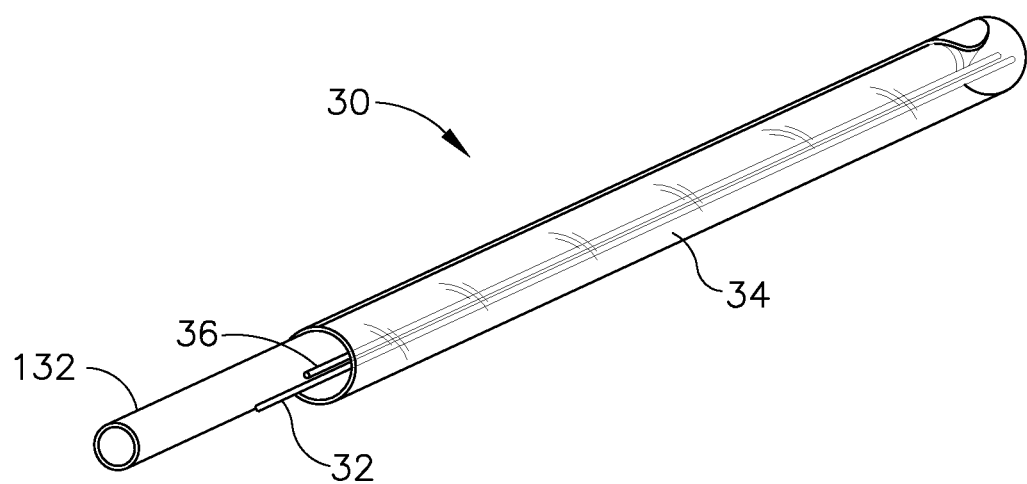
FIG. 3 depicts a perspective view of a shaft assembly of the instrument of FIG. 1.

As shown in FIG. 3, a plurality of cables (32) are disposed within shaft assembly (30). A proximal end of each cable (32) is secured to trigger (24) and a distal end of each cable is engaged with a respective wheel assembly (210, 180) in end effector (100). Trigger (24) is pivotable toward and away from pistol grip (22) to selectively translate cables (32) proximally within shaft assembly (30) to thereby rotate wheel assemblies (210, 180) and to thereby actuate end effector (100) as will be described in greater detail below. Cables (32) may be resiliently biased (32) distally. For instance, the distal ends of cables (32) may wrap about a portion of respective wheel assemblies (210, 180) and then be coupled with a spring disposed within shaft assembly (30). In addition or in the alternative, trigger (24) and/or wheel assemblies (210, 180) may be resiliently biased by torsion springs or other resilient members, which may effectively bias cables (32).

A cable (36) is also disposed within shaft assembly (30). A proximal end of cable (36) is secured to palm trigger (25) and a distal end of cable (36) is engaged with vacuum head (130). Palm trigger (25) is pivotable toward and away from pistol grip (22) to selectively translate cable (36) proximally within shaft assembly (30) to thereby move vacuum head (130) laterally from end effector (100) as will be described in greater detail below. Cable (36) may be resiliently biased such that cable (36) is biased distally. For instance, vacuum head (130) may be biased toward end effector such that cable (36) is biased distally. As another merely illustrative example, palm trigger (25) may be resiliently biased by a torsion spring or other resilient member, effectively biasing cable (36). It should be understood that pistol grip (22), trigger (24), and palm trigger (25) may be modified, substituted, supplemented, etc. in any suitable way, and that the descriptions of such components herein are merely illustrative. By way of example only, pistol grip (22), trigger (24), and/or palm trigger (25) may be configured and operable in accordance with at least some of the teachings of U.S. Pat. Pub. No. 2013/0153642, now U.S. Pat. No. 9,119,615, issued Sep. 1, 2015, the disclosure which is incorporated by reference herein. Other suitable modifications, substitutes, and supplements for pistol grip (22), trigger (24), and palm trigger (25) will be apparent to those of ordinary skill in the art in view of the teachings herein.

Figure 4:
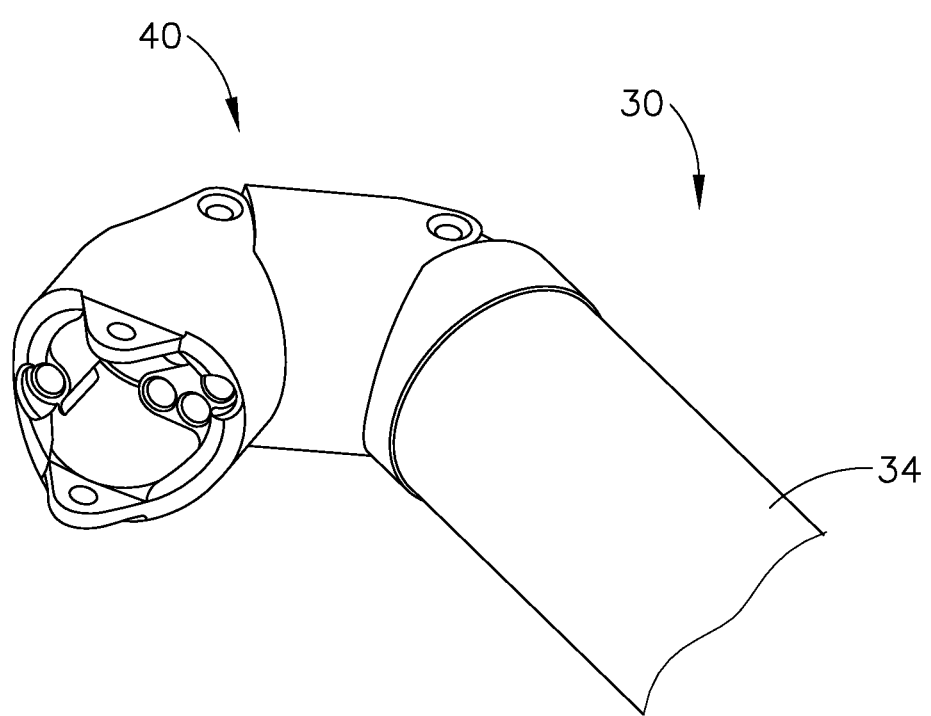
FIG. 4 depicts a perspective view of an articulation section of the instrument of FIG. 1.
Figure 5:
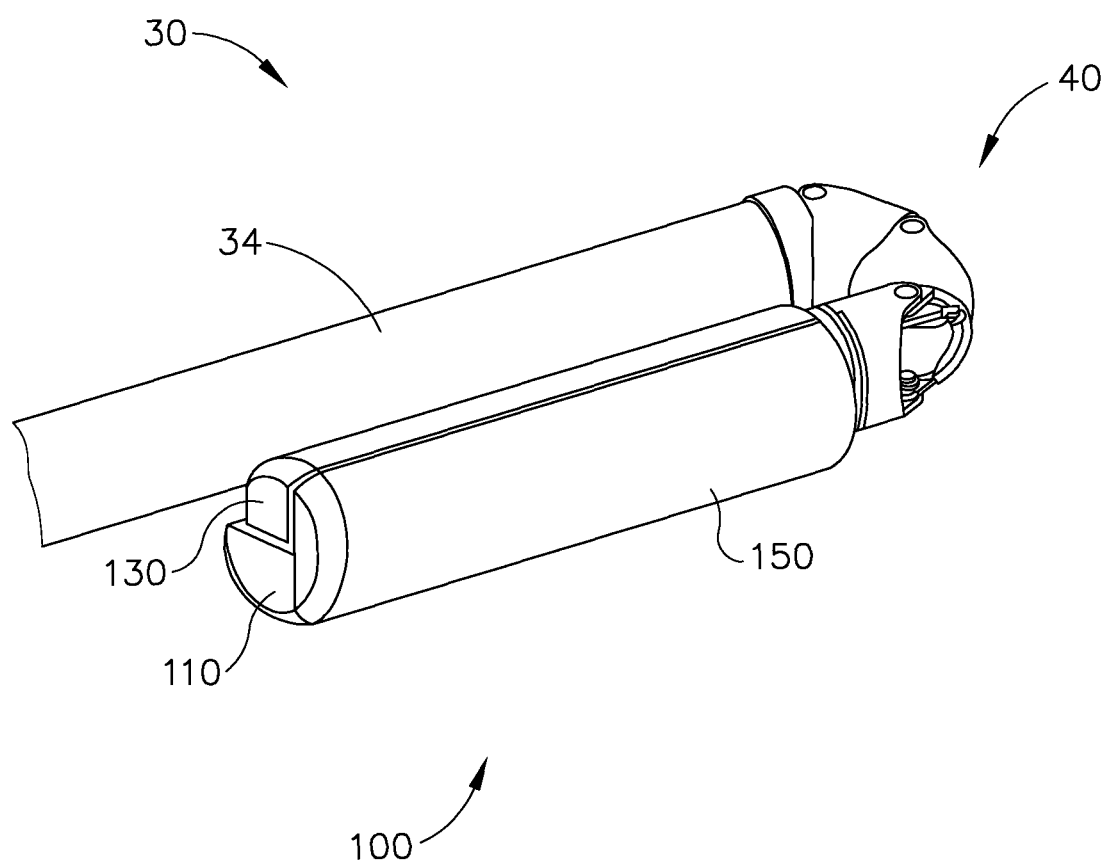
FIG. 5 depicts a perspective view of the shaft assembly, the articulation section, and the end effector of the instrument of FIG. 1.

As shown in FIGS. 1, 4, and 5 shaft assembly (30) of the present example is substantially flexible along its length and includes an outer sheath (34) and an articulation section (40). Articulation section (40) is operable to selectively laterally deflect end effector (100) at various angles relative to a longitudinal axis defined by outer sheath (34). As shown in FIGS. 1 and 5, articulation section (40) is configured to enable up to 180° deflection of end effector (100), such that end effector (100) has a retrograde orientation parallel to the longitudinal axis of shaft assembly (30), with end effector being laterally offset from the longitudinal axis of shaft assembly (30). Of course, this degree of articulation is merely optional. Articulation section (40) may instead be configured to enable articulation to any other suitable degree.

In some versions, articulation section (40) and/or some other portion of outer sheath (34) includes a flexible outer sheath (e.g., a heat shrink tube, etc.) disposed about its exterior. Articulation section (40) of shaft assembly (30) may take a variety of forms. By way of example only, articulation section (40) may be configured in accordance with at least some of the teachings of U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein. As another merely illustrative example, articulation section (40) may be configured in accordance with at least some of the teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. As yet another merely illustrative example, articulation section (40) may be configured in accordance with at least some of the teachings of U.S. Pat. Pub. No. 2013/0153642, now U.S. Pat. No. 9,119,615, issued Sep. 1, 2015, the disclosure of which is incorporated by reference herein. Various other suitable forms that articulation section (40) may take will be apparent to those of ordinary skill in the art in view of the teachings herein. It should also be understood that some versions of instrument (10) may simply lack articulation section (40).

In some versions, shaft assembly (30) is also rotatable about the longitudinal axis defined by sheath (34), relative to handpiece (20), via a rotation knob or some other feature (not shown). Such rotation may provide rotation of end effector (100) and shaft assembly (30) unitarily. In some other versions, the rotation knob is operable to rotate end effector (100) without rotating articulation section (40) or any portion of shaft assembly (30) that is proximal of articulation section (40). As another merely illustrative example, stapling instrument (10) may include one rotation control that provides rotatability of shaft assembly (30) and end effector (100) as a single unit; and another rotation control that provides rotatability of end effector (100) without rotating articulation section (40) or any portion of shaft (30) that is proximal of articulation section (40). Other suitable rotation schemes will be apparent to those of ordinary skill in the art in view of the teachings herein. Of course, rotatable features may simply be omitted if desired.

Articulation control knob (26) of the present example is operable to selectively control articulation section (40) of shaft assembly (30), to thereby selectively laterally deflect end effector (100) at various angles relative to the longitudinal axis defined by sheath (34). While articulation control knob (26) is in the form of a rotary dial in the present example, it should be understood that articulation control knob (26) may take numerous other forms. By way of example only, articulation control knob (26) and/or other components of handle assembly (20) may be constructed and operable in accordance with at least some of the teachings of U.S. Pub. No. 2012/0078243, entitled "Control Features for Articulating Surgical Device," published Mar. 29, 2012, the disclosure of which is incorporated by reference herein. As another merely illustrative example, articulation control knob (26) and/or other components of handle assembly (20) may be constructed and operable in accordance with at least some of the teachings of U.S. Pub. No. 2012/0078244, entitled "Control Features for Articulating Surgical Device," published Mar. 29, 2012, the disclosure of which is incorporated by reference herein. As still another merely illustrative example, articulation control knob (26) and/or other components of handle assembly (20) may be constructed and operable in accordance with at least some of the teachings of U.S. Pub. No. 2013/0023868, entitled "Surgical Instrument with Contained Dual Helix Actuator Assembly" published Jan. 24, 2013, now U.S. Pat. No. 9,545,253, issued Jan. 17, 2017, the disclosure of which is incorporated by reference herein. As yet another merely illustrative example, articulation control knob (26) and/or other components of handle assembly (20) may be constructed and operable in accordance with at least some of the teachings of U.S. Pat. Pub. No. 2013/0153642, now U.S. Pat. No. 9,119,615, issued Sep. 1, 2015, the disclosure of which is incorporated by reference herein. Still other suitable forms that articulation control knob (26) may take will be apparent to those of ordinary skill in the art in view of the teachings herein. It should also be understood that some versions of instrument (10) may simply lack an articulation control knob (26) or similar feature.

B. Exemplary End Effector

Figure 6:
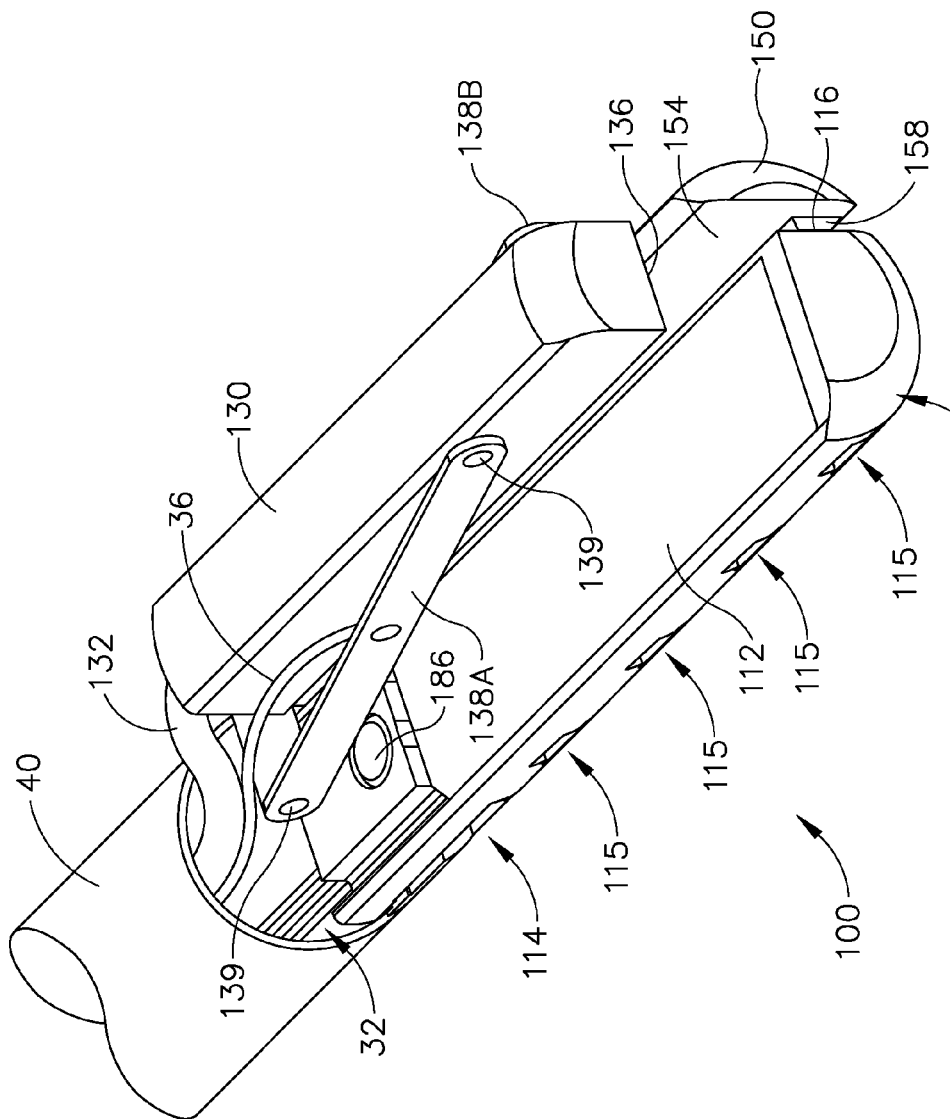
FIG. 6 depicts a perspective view of an exemplary end effector of the instrument of FIG. 1.
Figure 7:
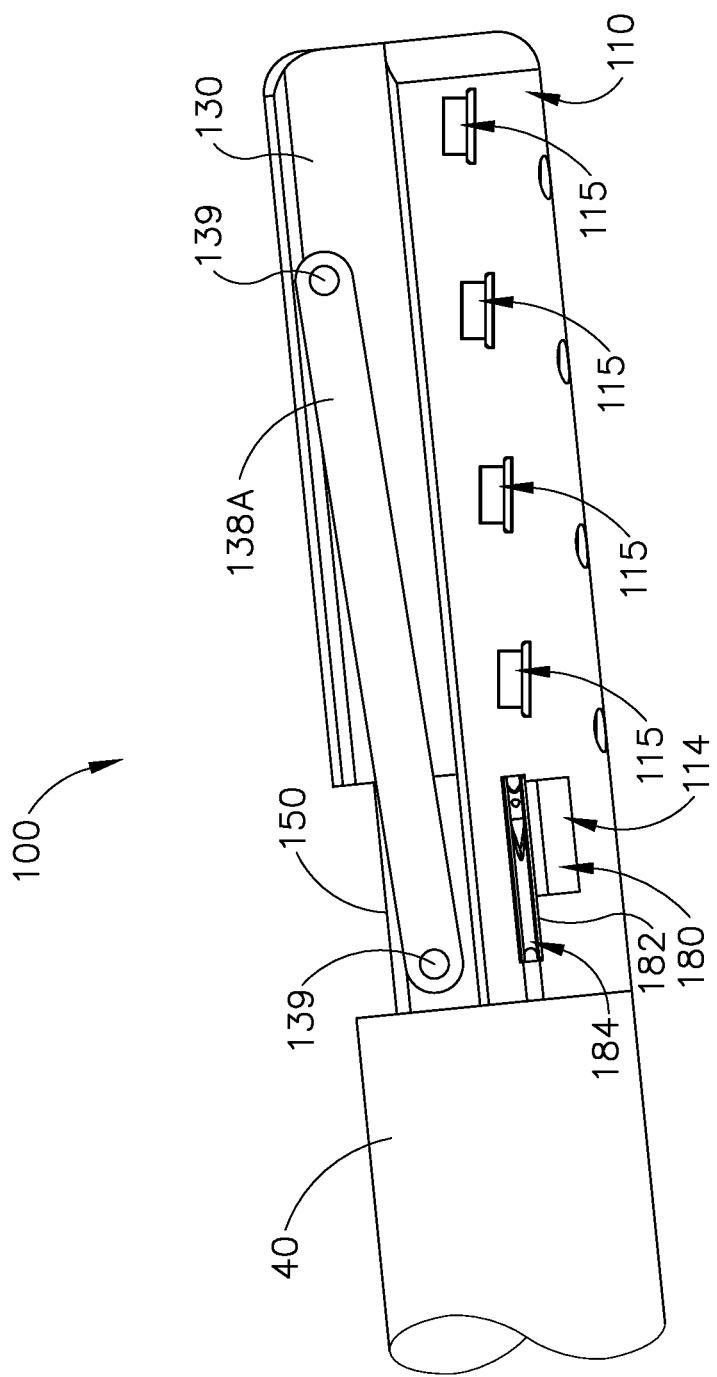
FIG. 7 depicts a side elevational view of the end effector of FIG. 6.
Figure 8:
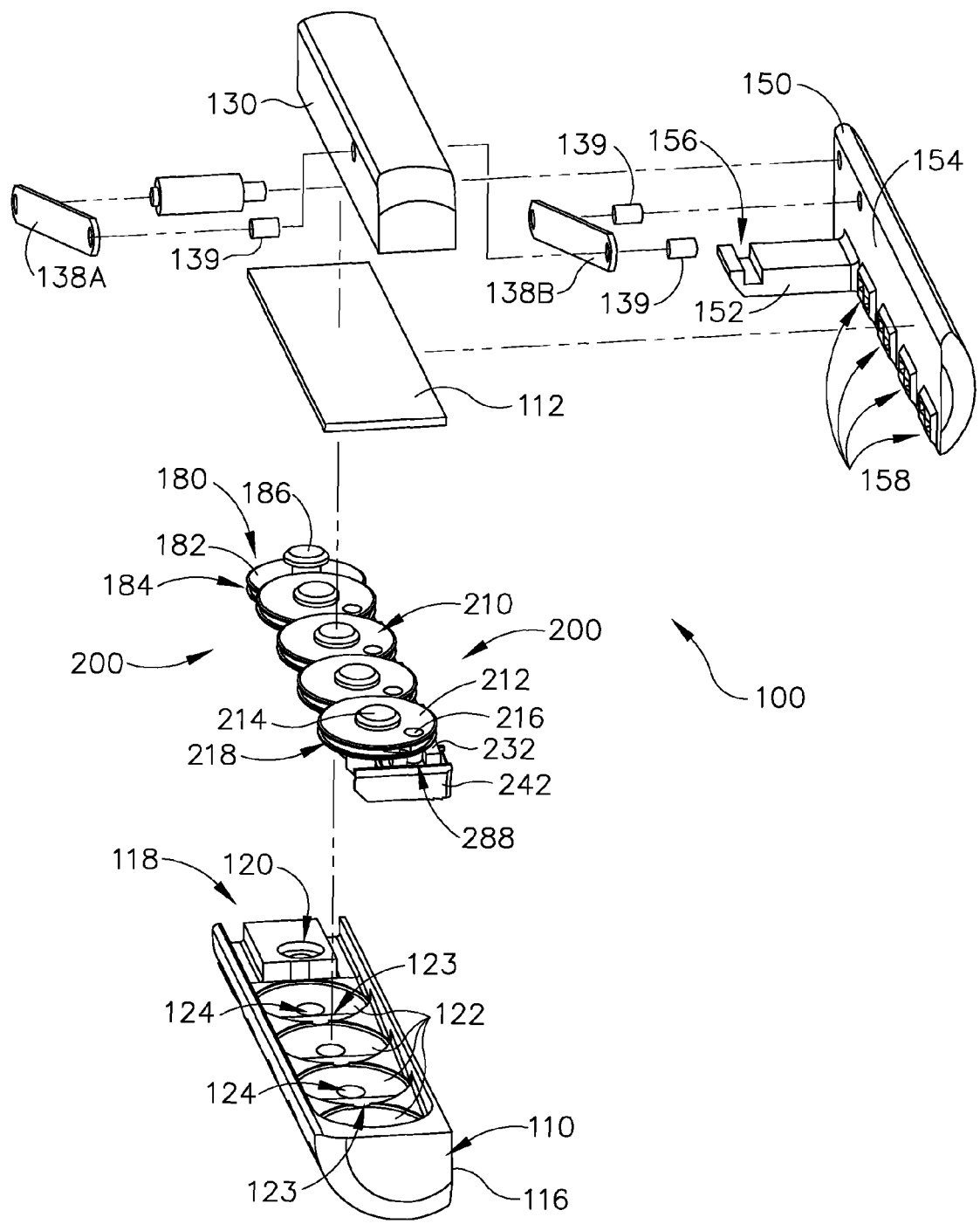
FIG. 8 depicts an exploded perspective view of the end effector of FIG. 6.

FIGS. 6-21G depict end effector (100) of the present example in greater detail. As shown in FIG. 6, end effector (100) of the present example is attached to a distal end of articulation section (40). End effector (100) comprises a stapling head assembly (110), a vacuum head (130), and an anvil (150). As best seen in FIG. 8, the interior of stapling head assembly (110) presents a longitudinal channel (118). As will be described in more detail below, wheel assemblies (180) of end effector (100) are disposed within longitudinal channel (118). Cover (112) is selectively attachable to stapling head assembly (110) such that cover (112) covers longitudinal channel (118) and wheel assemblies (180) as shown in FIG. 7. Such cover may prevent wheel assemblies (180) of end effector (100) from snagging on tissue as end effector (100) is inserted into a patient. Vacuum head (130) of the present example is operable to provide suction and thereby draw tissue (2) between anvil (150) and stapling head assembly (110). Wheel assemblies (210, 180) of the present example are operable to laterally drive anvil (150) toward and away from stapling head assembly (110), and to further drive staples (172) through tissue (2) that is compressed between anvil (150) and the deck (116) of stapling head assembly (110) as will be described in greater detail below.

1. Exemplary Anvil

Figure 9:
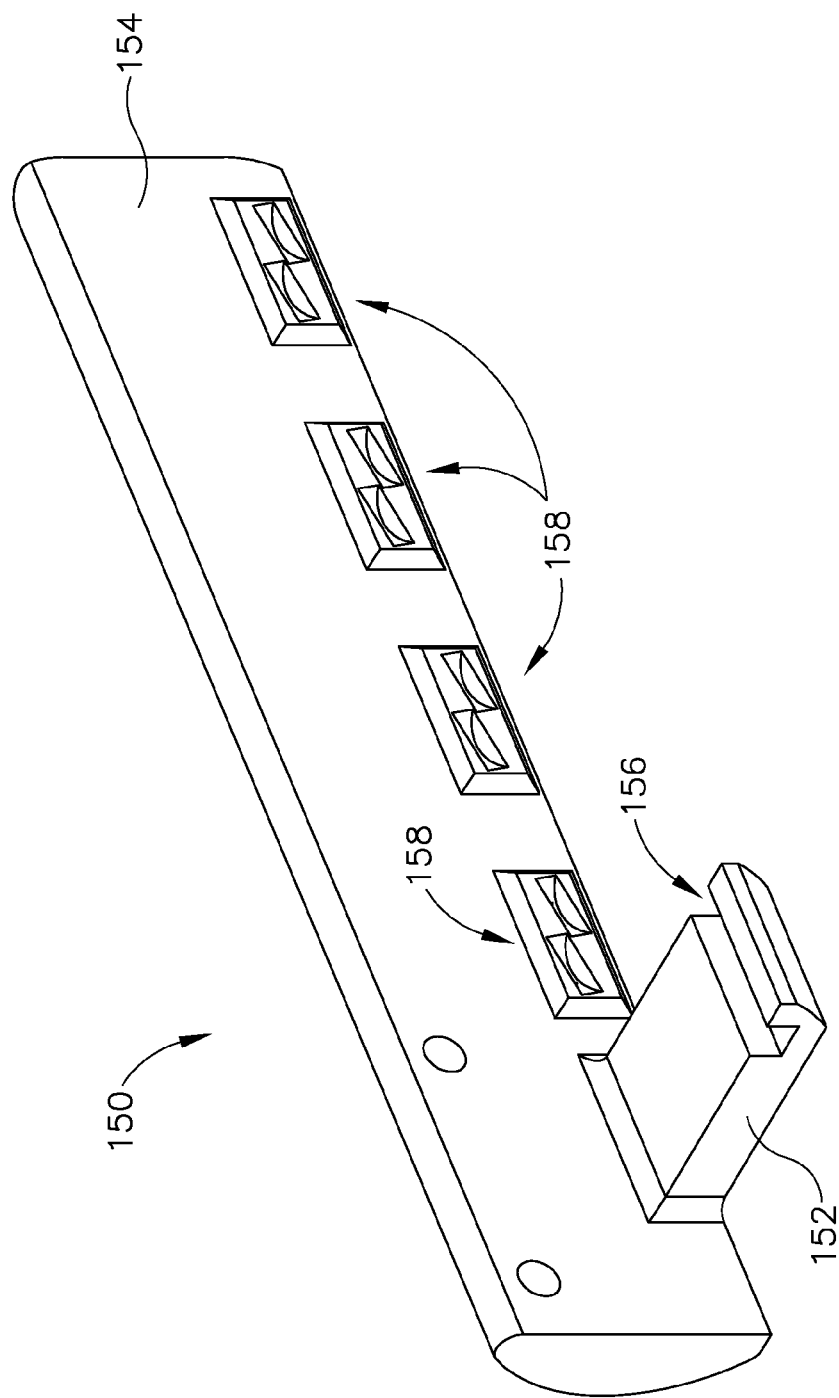
FIG. 9 depicts a perspective view of an anvil of the end effector of FIG. 6.
Figure 10:
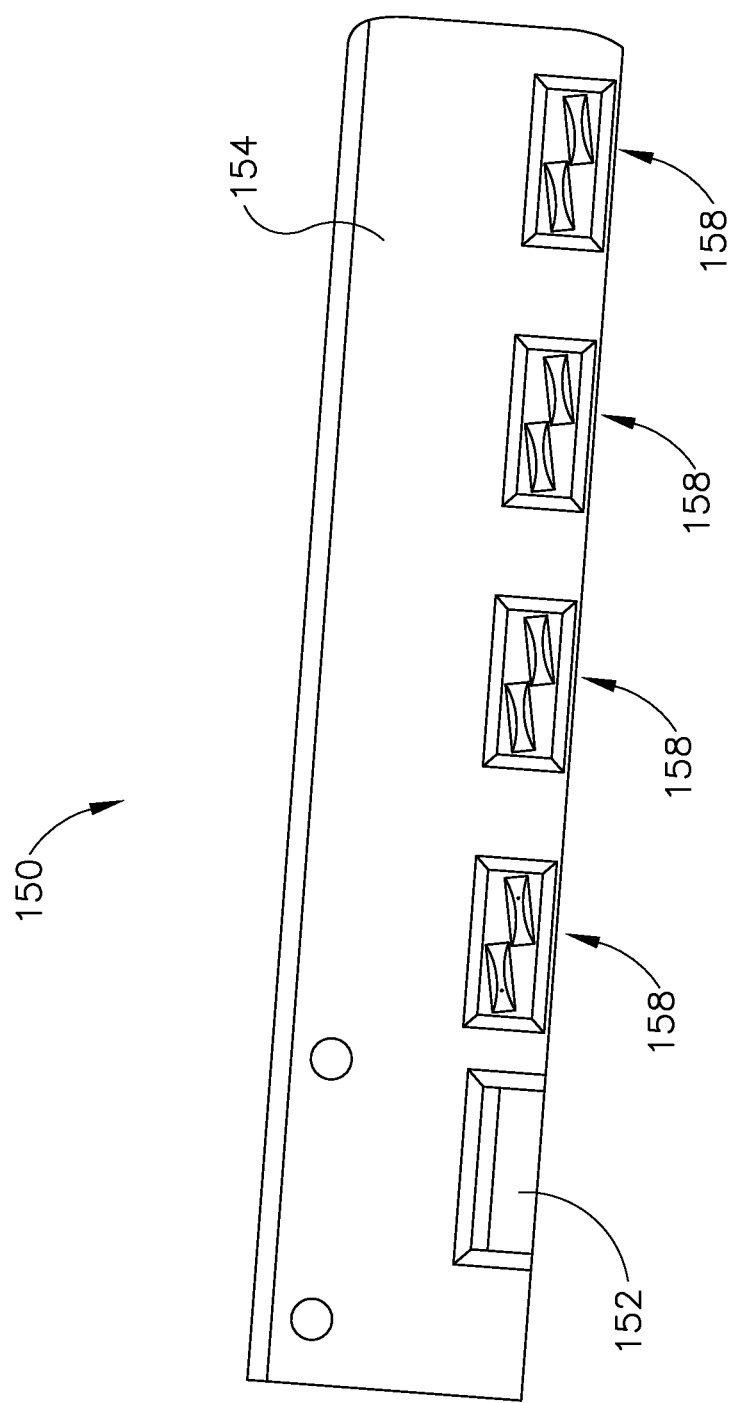
FIG. 10 depicts a side elevational view of the anvil of FIG. 9.
Figure 15:
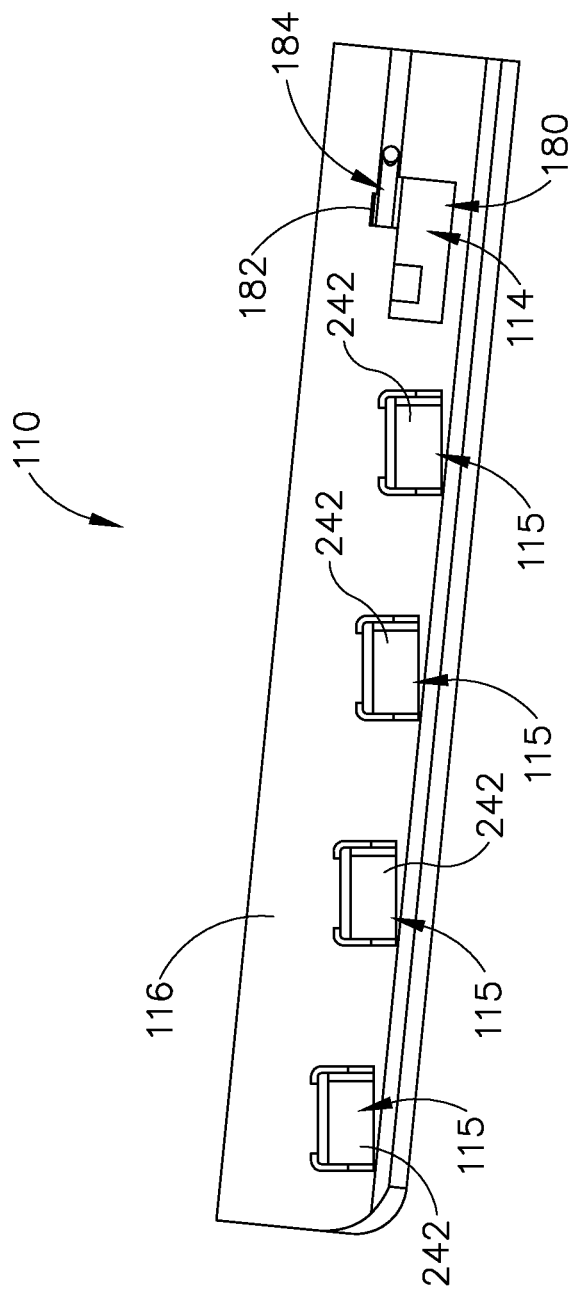
FIG. 15 depicts a side elevational view of a staple deck of the end effector of FIG. 6.
Figure 16:
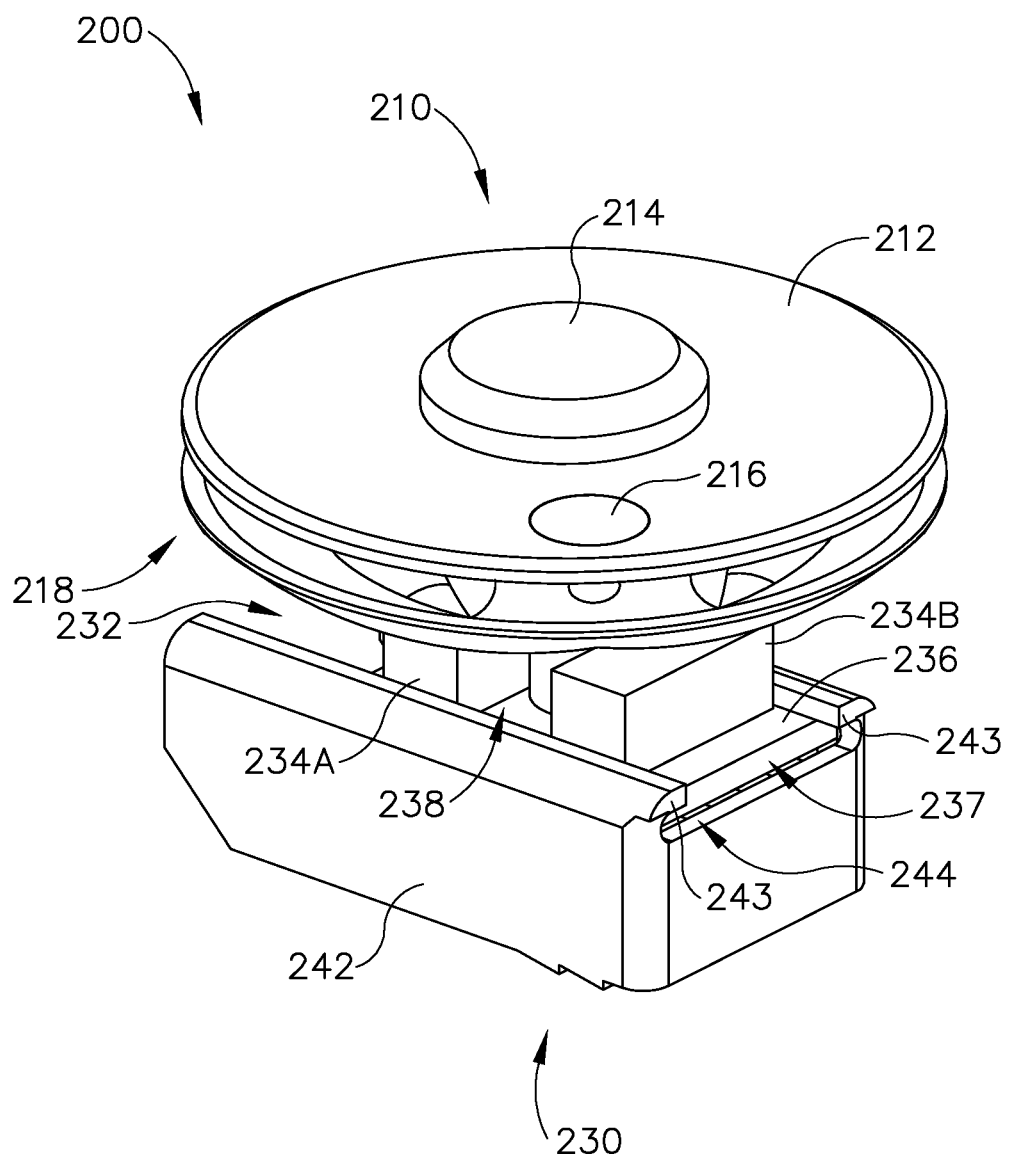
FIG. 16 depicts a perspective view of a stapling assembly of the end effector of FIG. 6.
Figure 17:
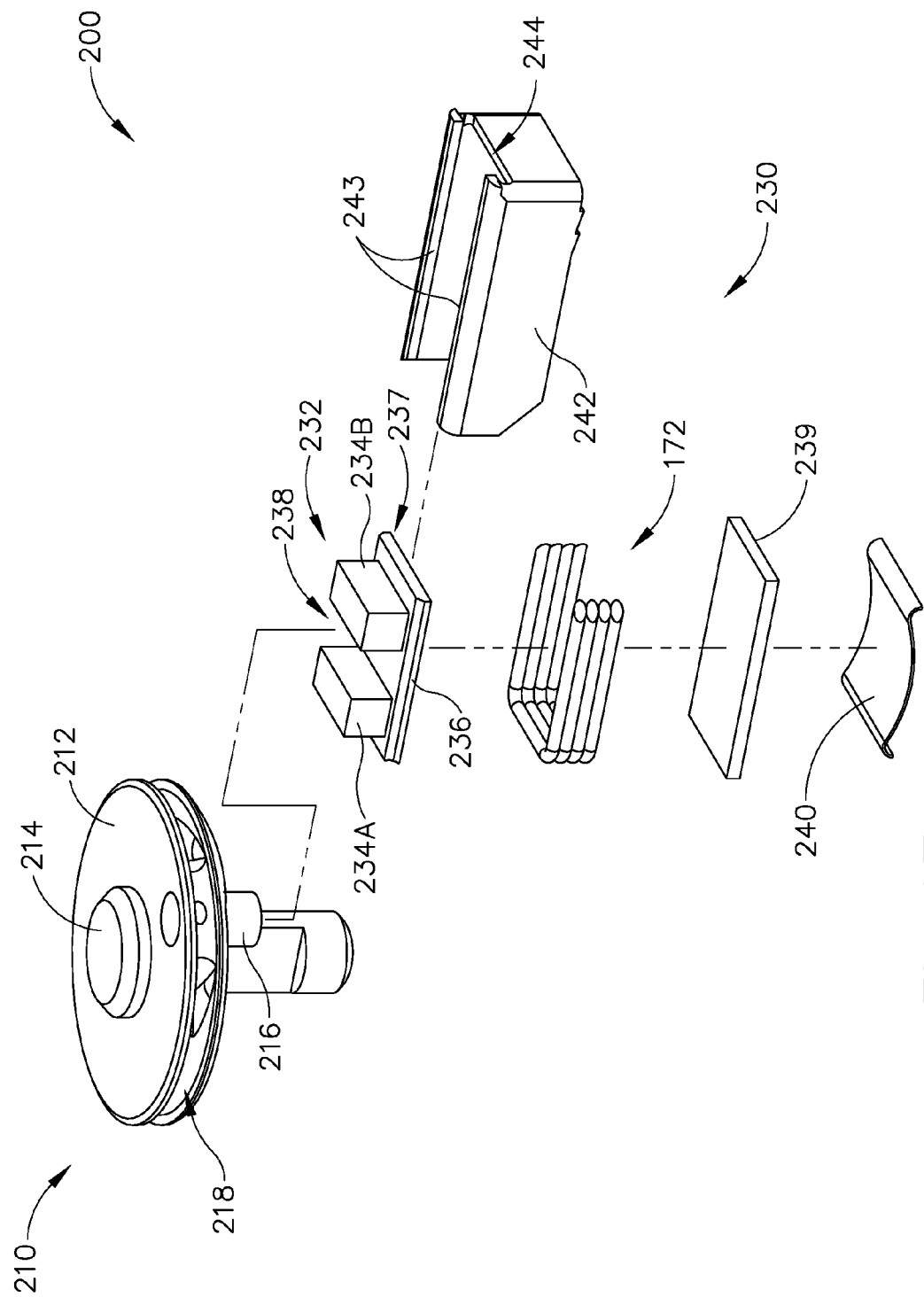
FIG. 17 depicts an exploded perspective view of the stapling assembly of FIG. 16.

FIGS. 9-10 depict anvil (150) in greater detail. An interior surface (154) of anvil (150) presents a plurality of staple forming pockets (158) that are configured to receive and form plurality of staples (172). As best seen in FIG. 10, staple forming pockets (158) are oriented obliquely relative to a longitudinal axis defined by stapling head assembly (110). By way of example only, staple forming pockets (158) may be formed according to the teachings of U.S. patent application Ser. No. 13/780,379, entitled "Staple Forming Features for Surgical Stapling Instrument," filed Feb. 28, 2013, now U.S. Pub. No. 2014/0239037, published Aug. 28, 2014, the disclosure of which is incorporated by reference herein. Alternatively, staple forming pockets (158) may have any other suitable configuration. An arm (152) projects laterally from a proximal end of interior surface (154) of anvil (150). As best seen in FIG. 15, a proximal end of stapling head assembly (110) presents a slot (114) that extends through deck (116) of stapling head assembly (110). Arm (152) is slidably disposed within slot (114) such that interior surface (154) of anvil (150) is operable to slide laterally toward and away from deck (116) of stapling head assembly (110), while maintaining a parallel relationship between anvil (150) and deck (116). Alternatively, anvil (150) may be pivotably connected to deck (116), with arm (152) being slidably disposed within slot (114) and pivotably connected to anvil (150) such that sliding arm (152) laterally toward and away from deck (116) maintains a non-parallel relationship between anvil (150) and deck (116). As will be discussed in more detail below, arm (152) defines a longitudinal channel (156) that spans the width of arm (152).

Figure 11:
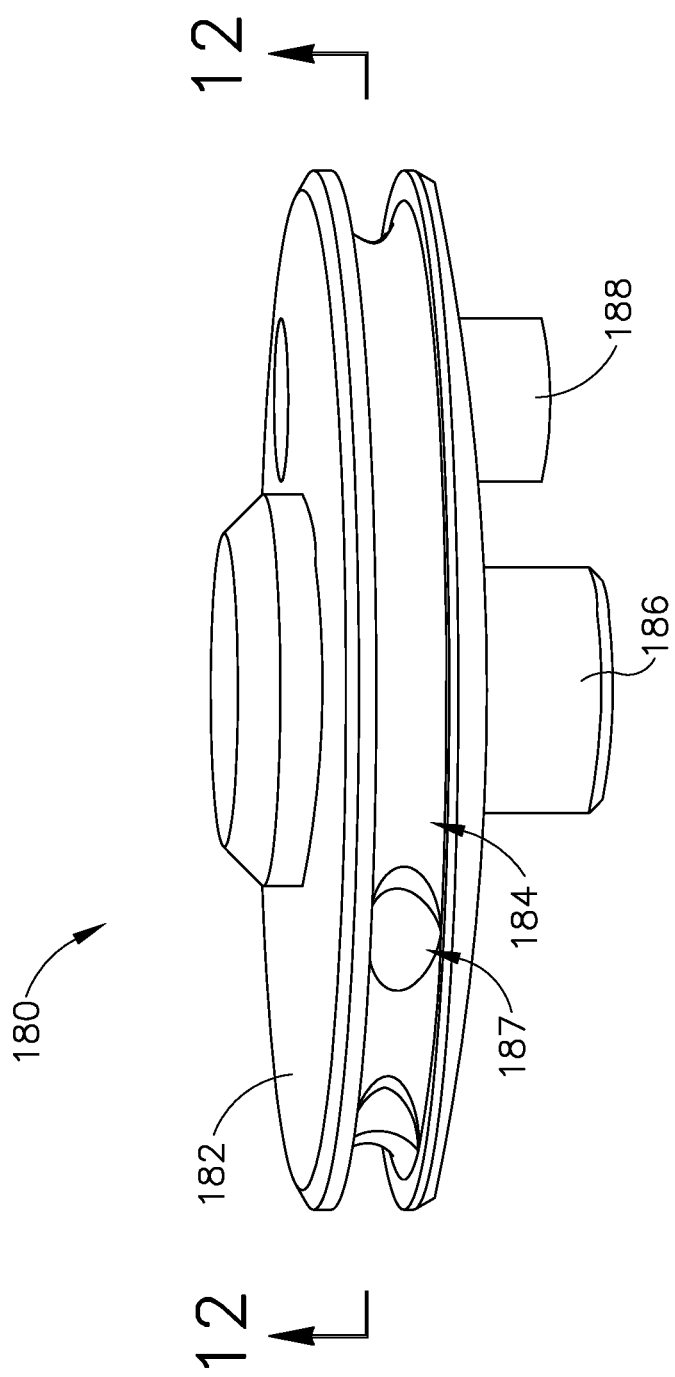
FIG. 11 depicts a perspective view of an exemplary wheel assembly of the end effector of FIG. 6.
Figure 12:
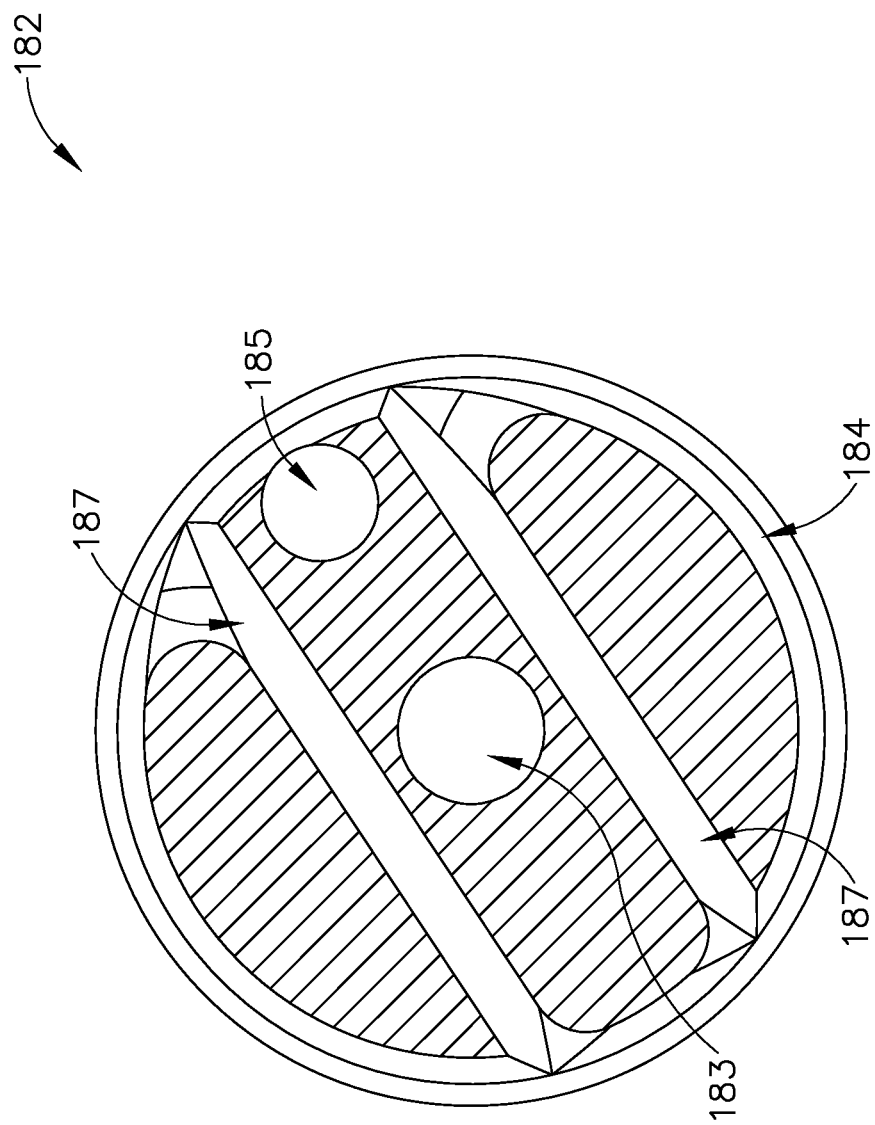
FIG. 12 depicts a cross-sectional view of the wheel assembly of FIG. 11, taken along line 12-12 of FIG. 11.

As best seen in FIGS. 11-12, an anvil wheel assembly (180) comprises a wheel (182), an axle (186), and a pin (188). Wheel (182) defines an annular channel (184) in an exterior surface of wheel (182). A pair of transverse retention channels (187) are in communication with annular channel (184). Annular channel (184) is configured to receive a cable (32A) of the plurality of cables (32), with an end of cable (32A) being secured in one or both of retention channels (187). It should therefore be understood that translation of cable (32A) will rotate wheel (182), based on the direction of translation of cable (32A). Axle (186) is secured within a central opening (183) of wheel (182) such that wheel (182) rotates about axle (186). Pin (188) is rotatably secured within an offset opening (185) of wheel (182) such that as wheel (182) rotates about axle (186), pin (188) orbits about axle (186). Pin (188) and axle (186) are oriented parallel to each other in this example.

A proximal end of stapling head assembly (110) defines a cavity that is configured to receive wheel (182). This cavity is in communication with slot (114), which is best seen in FIGS. 6-7. As best seen in FIG. 8, the proximal end of stapling head assembly (110) further defines an opening (120) that is configured to receive axle (186). Wheel assembly (180) is disposed within stapling head assembly (110) and slot (114) such that axle (186) is rotatably disposed within opening (120) and such that wheel assembly (180) rotates within stapling head assembly (110). Wheel assembly (180) is oriented such that pin (188) extends into longitudinal channel (156) of arm (152). Pin (188) is sized such that the diameter of pin (188) is slightly smaller than the width of longitudinal channel (156), such that pin (188) freely slides longitudinally within longitudinal channel (156) and such that there is very little gap between an exterior surface of pin (188) and interior surfaces of longitudinal channel (156). As will now be discussed in more detail, rotation of wheel assembly (180) is configured to cause lateral movement of anvil (150) relative to stapling head assembly (110).

Figure 13A:
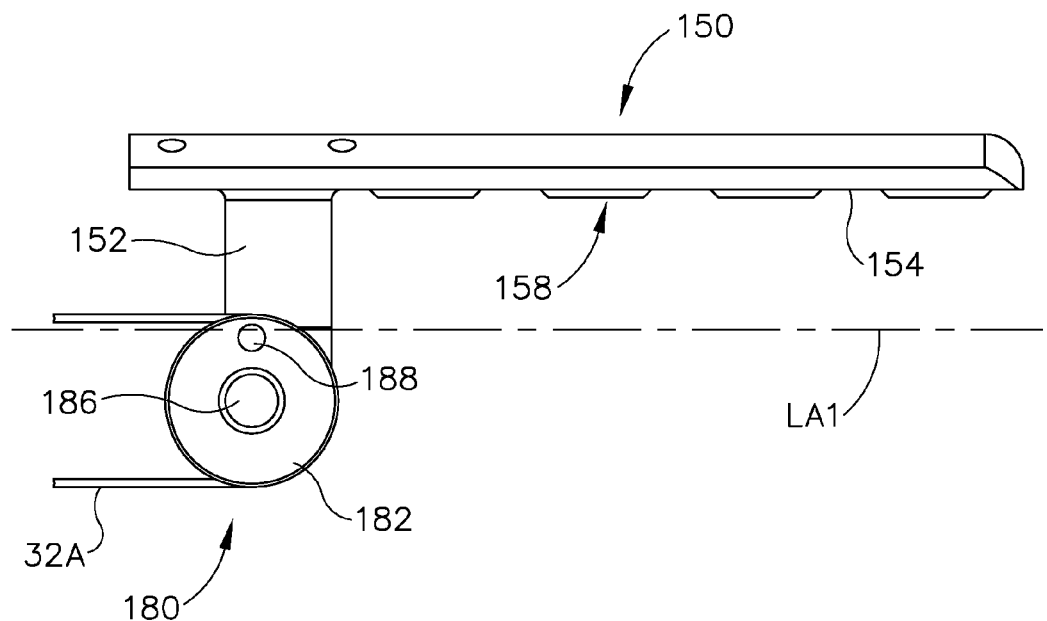
FIG. 13A depicts a top view of the wheel assembly of FIG. 11 and the anvil of FIG. 9 in a first position.

FIGS. 13A-13E depict the mechanical interaction of wheel assembly (180) and anvil (150). It should be understood that stapling head assembly (110) is omitted from FIGS. 13A-13E for the sake of clarity, though a longitudinal axis (LA1) shown in FIGS. 13A-13E represents where deck (116) of stapling head assembly (110) would be located. As shown in FIG. 13A, with pin (188) of wheel assembly (180) in a first rotational position relative to axle (186), anvil (150) is in a first lateral position relative to the deck (116) of stapling head assembly (110) as represented by longitudinal axis (LA1). This first lateral position represents a position in which interior surface (154) of anvil (150) is furthest from deck (116) of stapling head assembly (110). As will be discussed in more detail below, it is in this position that tissue (2) may be gathered between interior surface (154) of anvil (150) and deck (116) of stapling head assembly (110). Also, in this first rotational position, pin (188) is in a first longitudinal position relative to longitudinal channel (156) of arm (152). Finally, the first rotational position of wheel assembly (180) as shown in FIG. 13A correlates with trigger (24) being in a first pivotal position, where trigger (24) is pivoted furthest away from pistol grip (22).

Figure 13B:
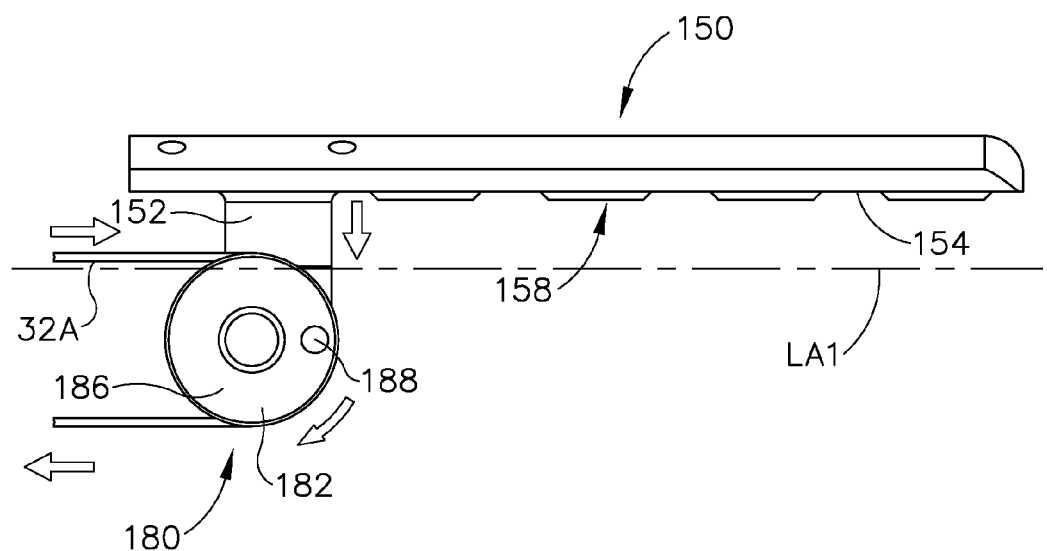
FIG. 13B depicts a top view of the wheel assembly of FIG. 11 and the anvil of FIG. 9 in a second position.

As trigger (24) is pivoted toward pistol grip (22), trigger (24) drives the plurality of cables (32) longitudinally proximally such that wheel assembly (180) is rotated clockwise approximately 90° to a second rotational position as shown in FIG. 13B. As pin (188) of wheel assembly (180) is rotated clockwise into the second rotational position, anvil (150) is transitioned to a second lateral position relative to the deck (116) of stapling head assembly (110) as represented by longitudinal axis (LA1), via contact between the exterior surface of pin (188) and a first interior surface of longitudinal channel (156) of arm (152). Furthermore, as pin (188) of wheel assembly (180) rotates from the first rotational position to the second rotational position, pin (188) slides longitudinally within longitudinal channel (156) from the first longitudinal position to a second longitudinal position. It should be understood that, the second rotational position of wheel assembly (180) correlates with a second pivotal position of trigger (24), where trigger (24) is pivoted approximately midway between the first pivotal position of trigger (24) and pistol grip (22).

Figure 13C:
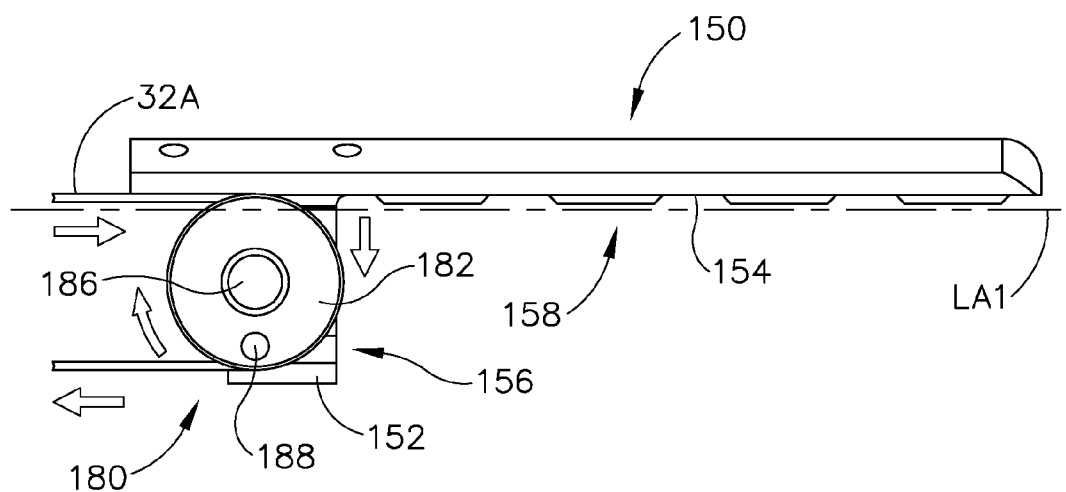
FIG. 13C depicts a top view of the wheel assembly of FIG. 11 and the anvil of FIG. 9 in a third position.

As trigger (24) is pivoted further toward pistol grip (22), trigger (24) further drives the plurality of cables (32) longitudinally proximally such that wheel assembly (180) is further rotated clockwise approximately 90° to a third rotational position as shown in FIG. 13C. As pin (188) of wheel assembly (180) is rotated clockwise into the third rotational position, anvil (150) is transitioned to a third lateral position relative to the deck (116) of stapling head assembly (110) as represented by longitudinal axis (LA1), via contact between the exterior surface of pin (188) and the first interior surface of longitudinal channel (156) of arm (152). This third lateral position represents a position in which interior surface (154) of anvil (150) is closest to deck (116) of stapling head assembly (110). As will be discussed in more detail below, it is in this third lateral position that tissue (2) will be compressed and stapled. Furthermore, as pin (188) of wheel assembly (180) rotates from the second rotational position to the third rotational position, pin (188) slides longitudinally within longitudinal channel (156) from the second longitudinal position back to the first longitudinal position. It should be understood that the third rotational position of wheel assembly (180) correlates with a third pivotal position of trigger (24), where trigger (24) is closest to pistol grip (22).

Figure 13D:
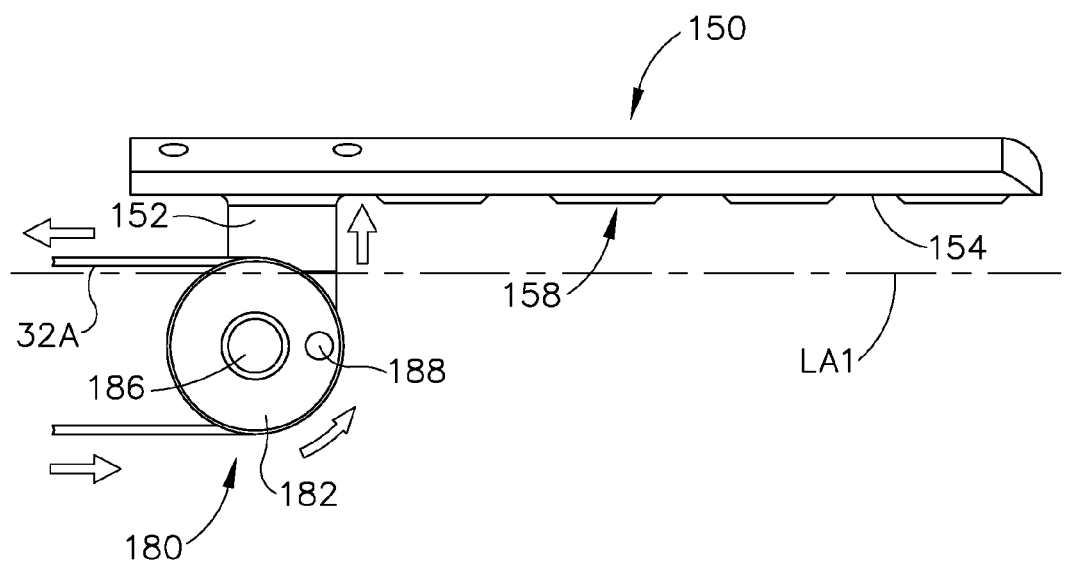
FIG. 13D depicts a top view of the wheel assembly of FIG. 11 and the anvil of FIG. 9 returned to the second position.

Once trigger (24) is released, the distal bias applied to cables (32) drives trigger (24) away from pistol grip (22), and cables (32) are driven distally such that wheel assembly (180) is rotated counter-clockwise approximately 90° back to the second rotational position as shown in FIG. 13D. As pin (188) of wheel assembly (180) is rotated counter-clockwise back to the second rotational position, anvil (150) is transitioned back to the second lateral position relative to the deck (116) of stapling head assembly (110) as represented by longitudinal axis (LA1), via contact between the exterior surface of pin (188) and a second interior surface of longitudinal channel (156) of arm (152). Furthermore, as pin (188) of wheel assembly (180) rotates from the third rotational position back to the second rotational position, pin (188) slides longitudinally within longitudinal channel (156) from the first longitudinal position to the second longitudinal position. Again, the second rotational position of wheel assembly (180) correlates with the second pivotal position of trigger (24), where trigger (24) is approximately midway between the first pivotal position of trigger (24) and pistol grip (22).

Figure 13E:
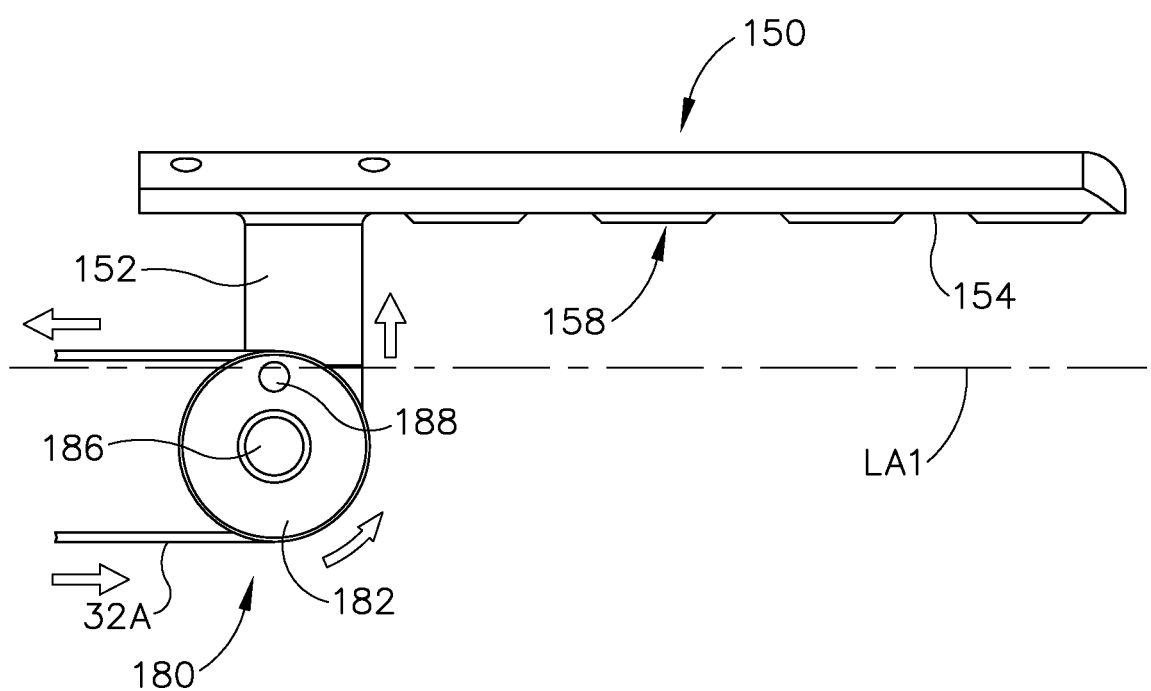
FIG. 13E depicts a top view of the wheel assembly of FIG. 11 and the anvil of FIG. 9 returned to the first position.

As trigger (24) is further driven away from pistol grip (22) via cables (32), cables (32) are further driven longitudinally distally such that wheel assembly (180) is further rotated counter-clockwise approximately 90° back to the first rotational position as shown in FIG. 13E. As pin (188) of wheel assembly (180) is rotated counter-clockwise back to the first rotational position, anvil (150) is transitioned back to the first lateral position relative to the deck (116) of stapling head assembly (110) as represented by longitudinal axis (LA1), via contact between the exterior surface of pin (188) and the second interior surface of longitudinal channel (156) of arm (152). Again, this first lateral position represents a position in which interior surface (154) of anvil (150) is furthest from deck (116) of stapling head assembly (110). Furthermore, as pin (188) of wheel assembly (180) rotates from the second rotational position back to the first rotational position, pin (188) is slid longitudinally within longitudinal channel (156) from the second longitudinal position back to the first longitudinal position. Again, the first rotational position of wheel assembly (180) correlates with trigger (24) being in the first pivotal position, where trigger (24) is furthest from pistol grip (22).

It should be understood from the foregoing that movement of trigger (24) from the first pivotal position to the third pivotal position and back to the first pivotal position, will drive anvil (150) from the first lateral position to the third lateral position and back to the first lateral position. It should also be understood that anvil (150) may alternatively be driven using a variety of other structures, features, and techniques. Various examples of such alternatives will be apparent to those of ordinary skill in the art in view of the teachings herein.

2. Exemplary Vacuum Head

FIGS. 14A-14D and FIGS. 20A-20E depict exemplary operation of vacuum head (130). Vacuum head (130) defines an inner lumen (not shown) that connects to one or more vacuum openings (not shown) formed in a tissue engaging surface (134) of vacuum head (130). A vacuum lumen (132) passes longitudinally through shaft assembly (30) and articulation section (40) and is in fluid communication with the inner lumen of vacuum head (130) such that a vacuum is communicated to the vacuum openings of tissue engaging surface (134) and such that the vacuum openings are operable to engage and draw tissue against tissue engaging surface (134) of vacuum head (130). As will be discussed in more detail below, this vacuum is further operable to cause vacuum head (130) to draw tissue into a gap defined between anvil (150) and deck (116) of stapling head assembly (110).

Vacuum head (130) of the present example is pivotally coupled with interior surface (154) of anvil (150) via a plurality of hinge members (138A, 138B). Hinge members (138A, 138B) of the present example comprise a first hinge member (138A) and a second hinge member (138B). First hinge member (138A) is pivotally connected at one end to a distal end of vacuum head (130); and pivotally connected at the other end to a proximal end of anvil (150). Second hinge member (138B) is pivotally connected at one end to a distal end of vacuum head (130); and pivotally connected at the other end to a proximal end of anvil (150). Hinge members (138A, 138B) are coupled on opposite sides of vacuum head (130). Additionally, hinge members (138A, 138B) may be offset longitudinally relative to each other. The pivotal connection between hinge members (138A, 138B) and vacuum head (130) and anvil (150) can be accomplished using, for example, a plurality hinge pins (139). Hinge members (138A, 138B) allow vacuum head (130) to be driven toward and away from stapling head assembly (110) while maintaining tissue engaging surface (134) at an orientation that is substantially parallel to stapling head assembly (110). There may also be some associated proximal/distal longitudinal motion because hinge members (138A, 138B) drive vacuum head (130) along an arcuate path. In particular hinge members (138A, 138B) can allow vacuum head (130) to move from the position shown in FIG. 14C to the position shown in FIG. 14D and further to the position shown in FIG. 20B without changing the substantially parallel orientation of vacuum head (130).

Figure 14A:
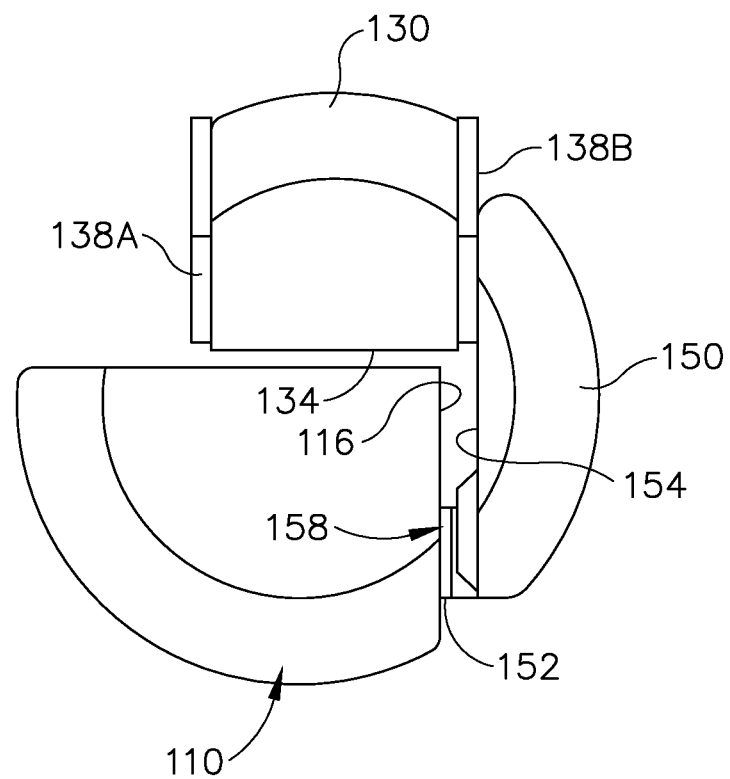
FIG. 14A depicts a front elevational view of the end effector of FIG. 6 with the anvil of FIG. 9 in the third position and with a vacuum port in a first position.
Figure 14B:
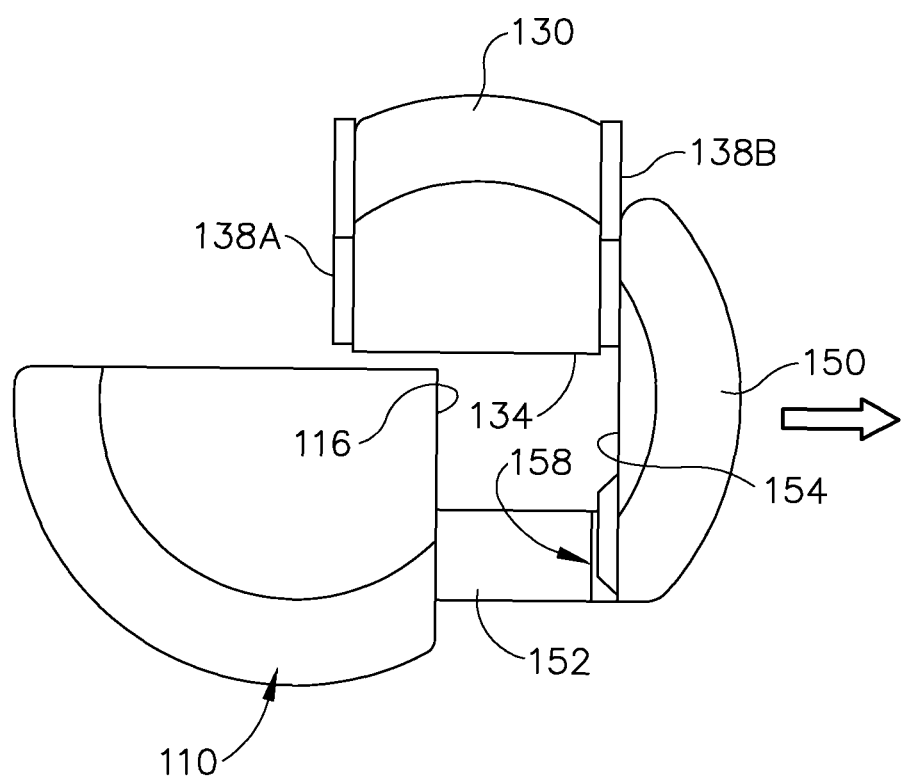
FIG. 14B depicts a front elevational view of the end effector of FIG. 6 with the anvil of FIG. 9 in the second position and with the vacuum port in the first position.
Figure 14C:
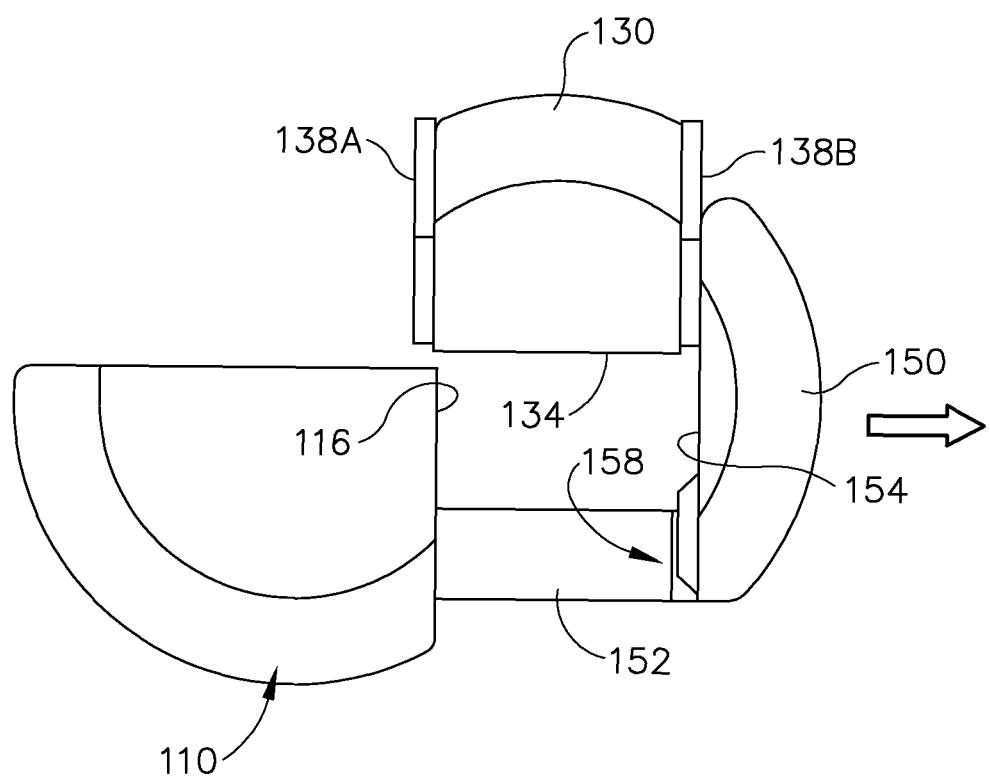
FIG. 14C depicts a front elevational view of the end effector of FIG. 6 with the anvil of FIG. 9 in the first position and with the vacuum port in the first position.
Figure 14D:
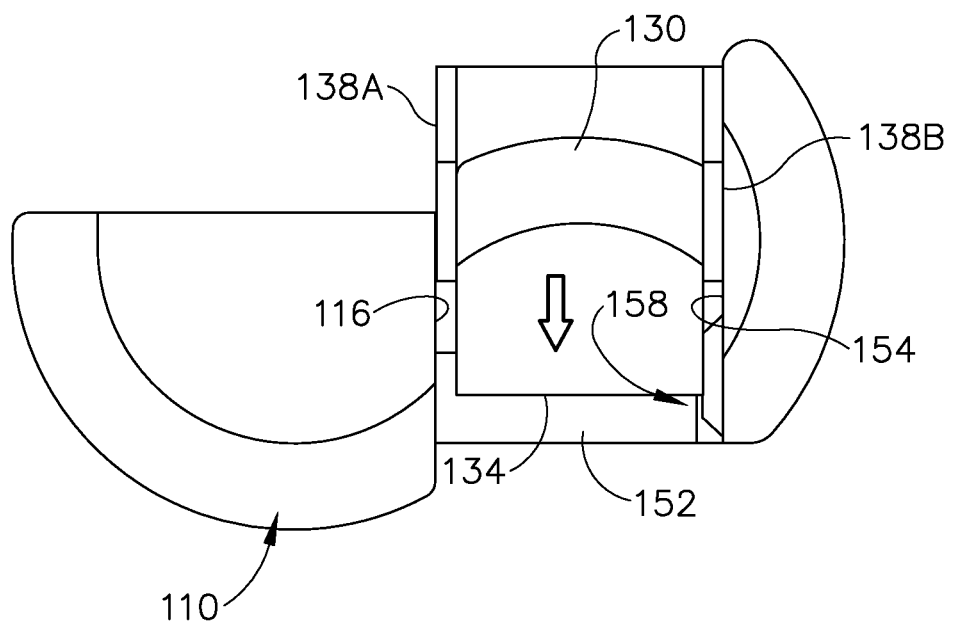
FIG. 14D depicts a front elevational view of the end effector of FIG. 6 with the anvil of FIG. 9 in the first position and with the vacuum port in a second position.
Figure 20A:
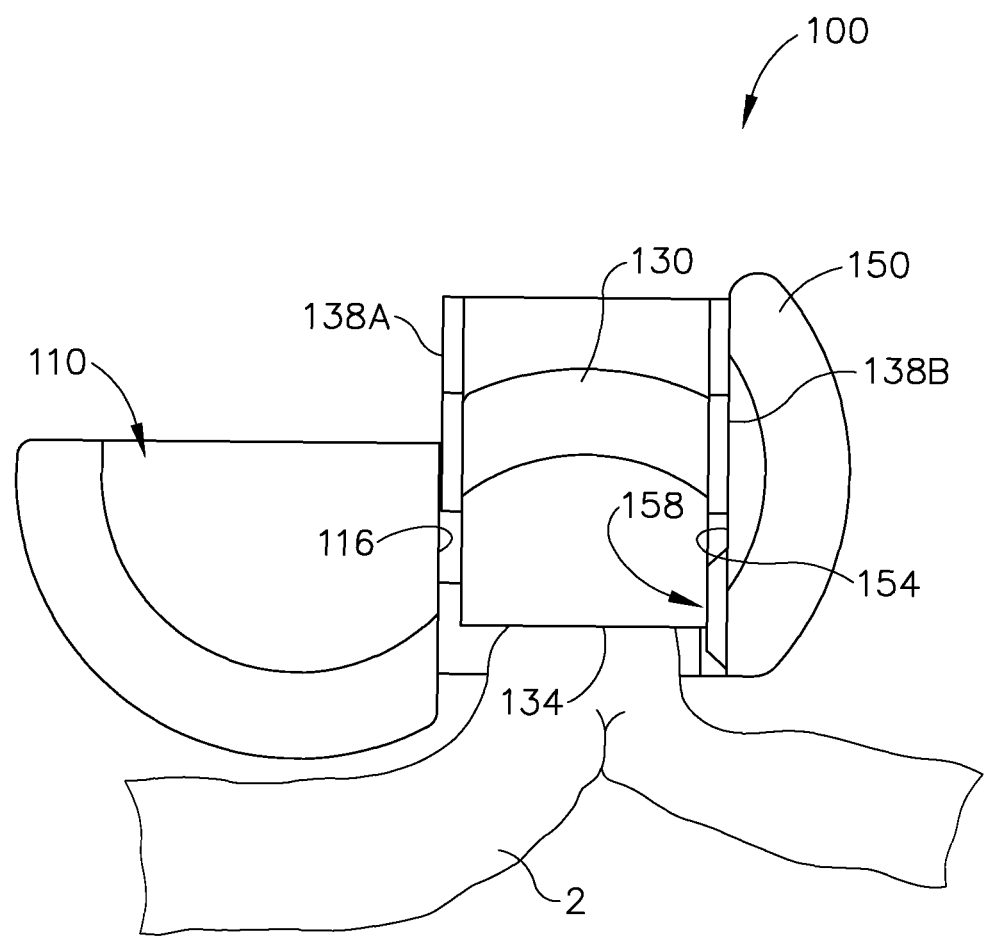
FIG. 20A depicts a front elevational view of the end effector of FIG. 6 with the anvil of FIG. 9 in the first position and with the vacuum port in the second position, adjacent to tissue.
Figure 20B:
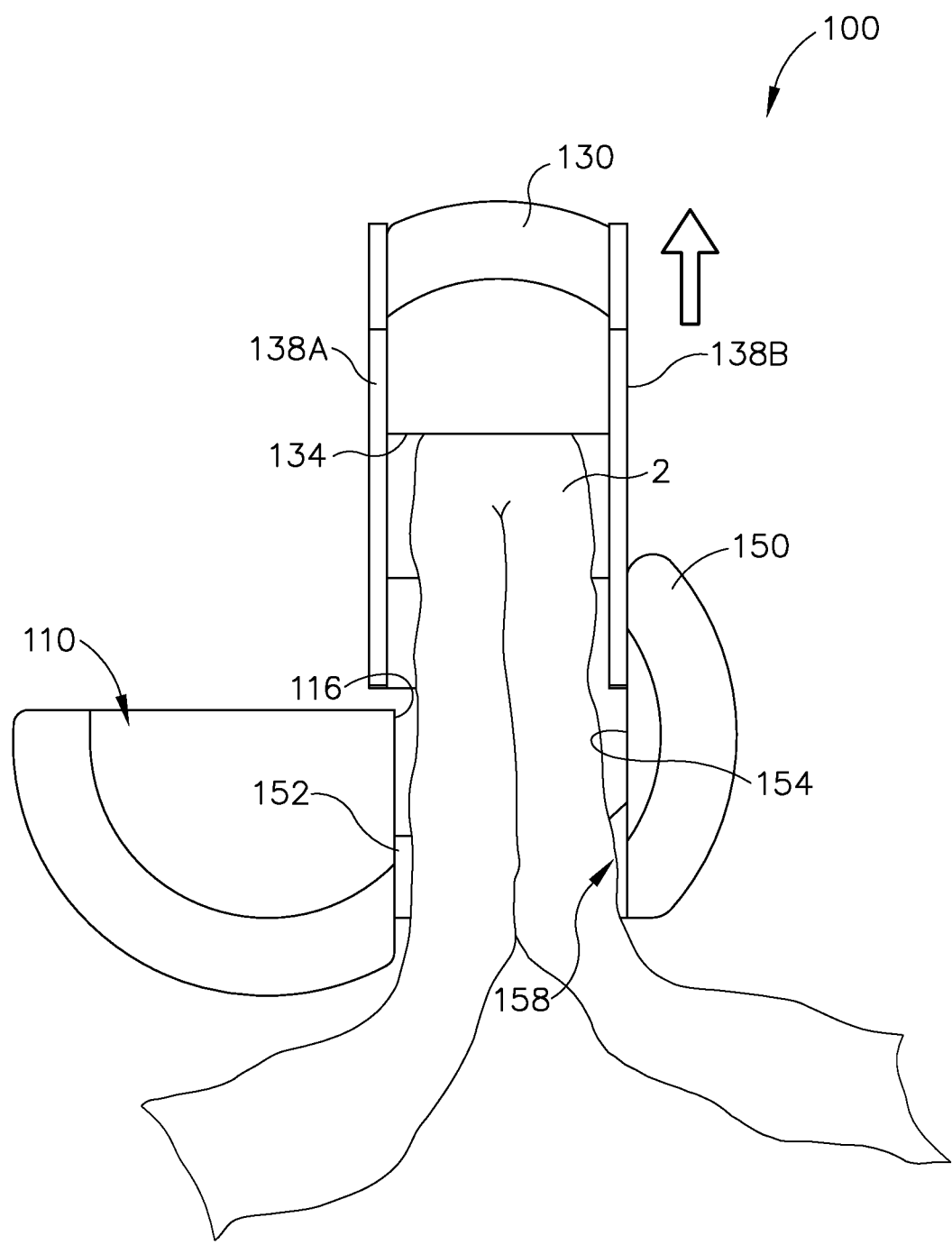
FIG. 20B depicts a front elevational view of the end effector of FIG. 6 with the anvil of FIG. 9 in the first position and with the vacuum port in a third position, pulling tissue between the anvil and the staple deck of the end effector.
Figure 20C:
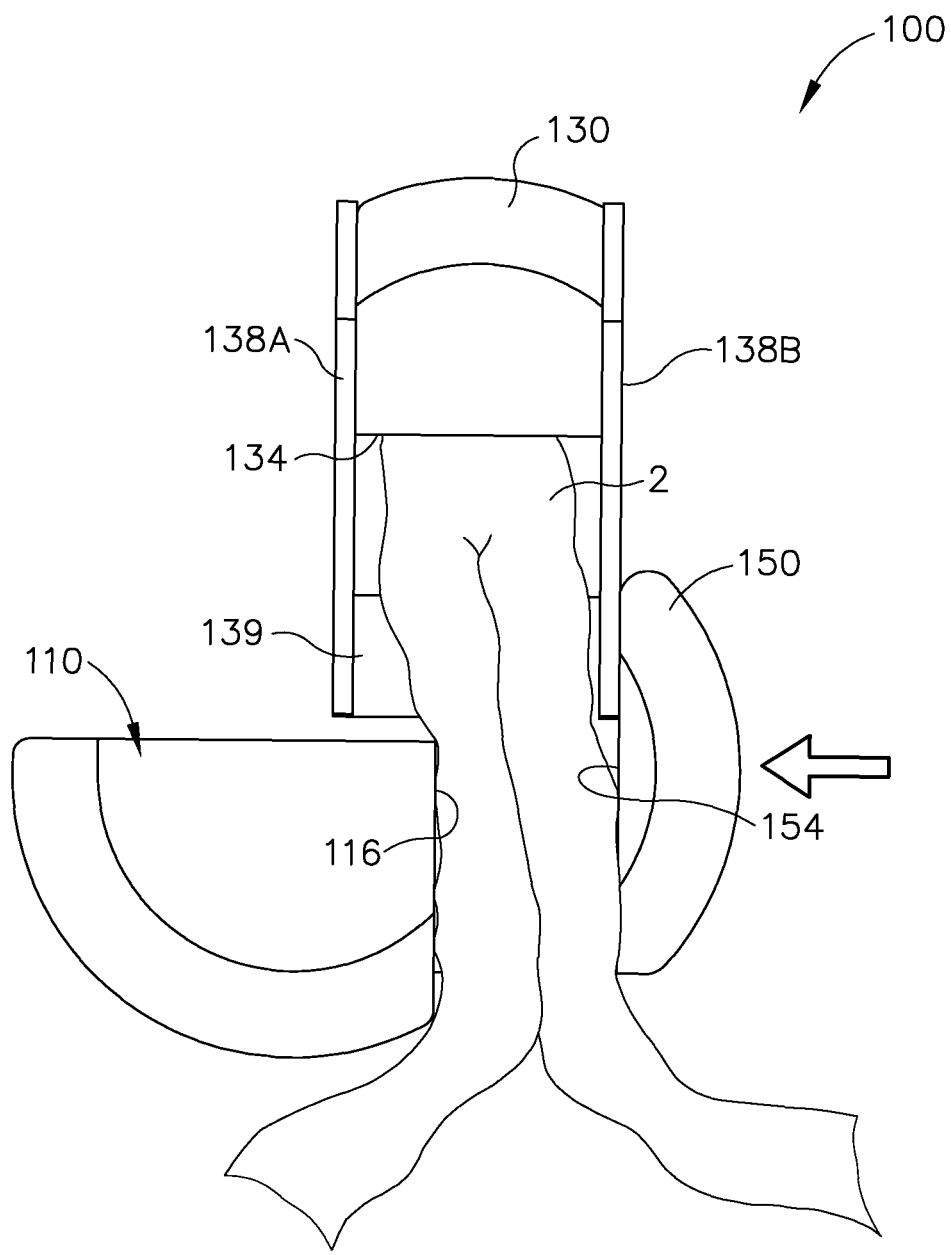
FIG. 20C depicts a front elevational view of the end effector of FIG. 6 with the anvil of FIG. 9 returned to the second position, beginning to compress the tissue between the anvil and the staple deck, and with the vacuum port in the third position.
Figure 20D:
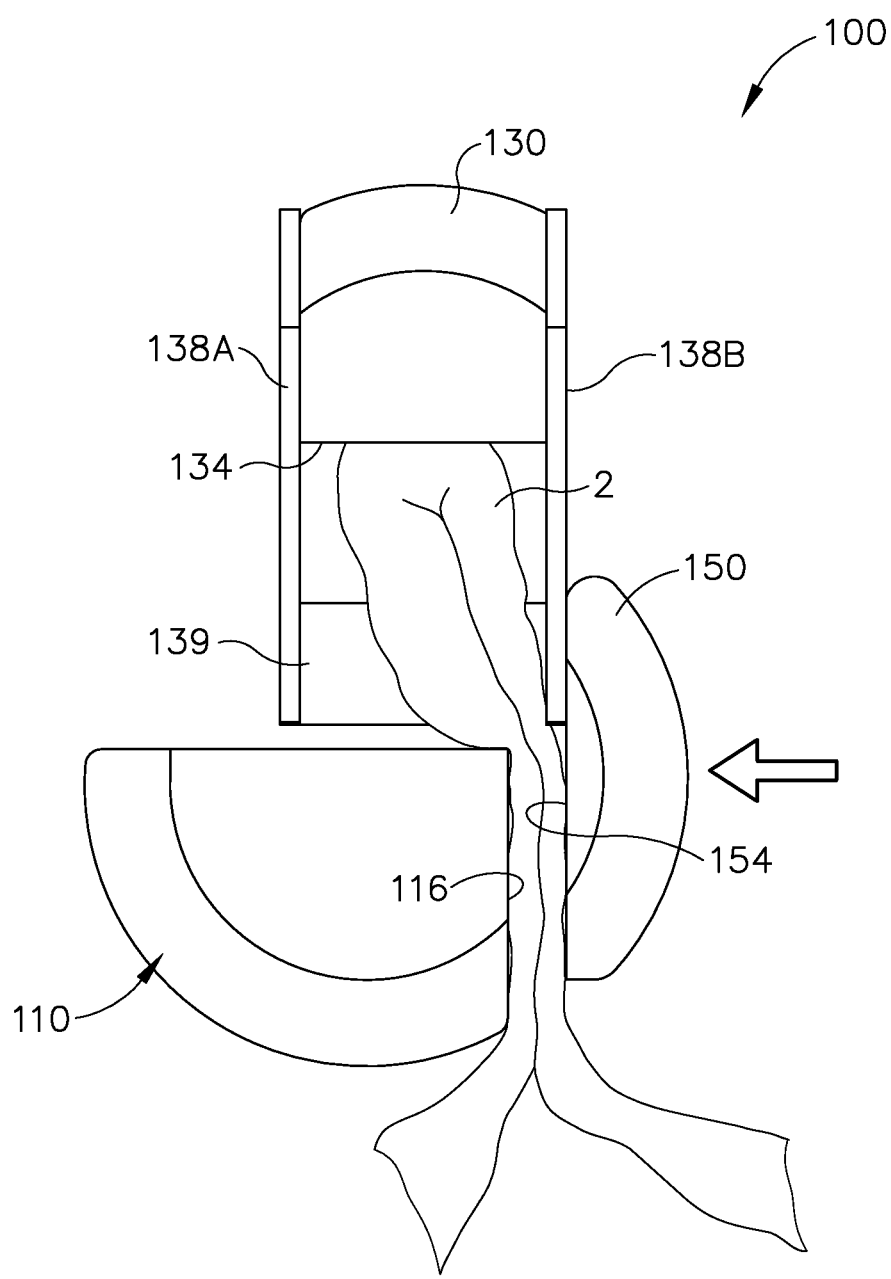
FIG. 20D depicts a front elevational view of the end effector of FIG. 6 with the anvil of FIG. 9 returned to the third position, fully compressing the tissue between the anvil and the staple deck, and with the vacuum port in the third position.

As shown in the series depicted in FIGS. 14A-14C, as anvil (150) is driven from the third lateral position to the first lateral position, vacuum head (130) is concurrently driven from the third lateral position to the first lateral position because vacuum head (130) is coupled to anvil (150). As also best seen in FIGS. 14C-14D, vacuum head (130) is sized such that vacuum head (130) fits within the gap defined by interior surface (154) of anvil (150) and deck (116) of stapling head assembly (110) when anvil (150) is in the first lateral position. As shown in FIG. 14D, with anvil (150) in the first lateral position, vacuum head (130) can be driven downwardly within the gap defined by interior surface (154) of anvil (150) and deck (116) of stapling head assembly (110) from a first vertical position to a second vertical position. Vacuum head (130) may be biased downwardly toward the second position, for example, by a plurality of linear and/or torsion springs associated with hinge members (138A, 138B). As will be discussed in more detail below, in the second vertical position, a vacuum source can be activated and vacuum head (130) may thereby draw tissue (2) against tissue engaging surface (134) of vacuum head (130). Palm trigger (25) may be pivoted toward pistol grip (22) to draw cable (36) proximally, to thereby raise vacuum head (130) and draw tissue (2) from the second vertical position to a third vertical position through the gap between interior surface (154) of anvil (150) and deck (116) of stapling head assembly (110), thereby creating a gastric fold as shown in FIG. 20B. Also, as will be discussed in more detail below, anvil (150) can then be driven back to the first position and one or more staples (172) can be fired to secure the plication.

3. Exemplary Stapling Assemblies

Stapling head assembly (110) of the present example comprises plurality of stapling assemblies (200). While stapling head assembly (100) includes four stapling assemblies (200) in the present example, it should be understood that any other suitable number of stapling assemblies (200) may be incorporated into stapling head assembly (110). As shown in FIGS. 16-19E, each stapling assembly (200) comprises a wheel assembly (210) and a staple cartridge (230). Wheel assembly (210) comprises a wheel (212), an axle (214), and a pin (216). Wheel (212) comprises a circular channel (218) defined in an exterior surface of wheel (212). Circular channel (218) is configured to receive a cable of the plurality of cables (32). It should be understood that wheels (212) are engaged with respective cables (32) similar to the engagement of wheel (182) with cable (32A). Translation of cables (32) is thus configured to rotate corresponding wheels (212). Axle (214) is secured within a central opening of wheel (212) such that wheel (212) rotates about axle (214). Pin (216) is rotatably secured within an offset opening of wheel (212) such that as wheel (212) rotates about axle (214), pin (216) also orbits about axle (214). Pin (216) and axle (214) are oriented parallel to each other in this example.

As shown in FIG. 15, deck (116) of stapling head assembly (110) presents a plurality of slots (115) that extend laterally through stapling head assembly (110). Slots (115) are oriented obliquely at angles similar to the angles at which staple forming pockets (158) are obliquely oriented. It should be understood that each slot of the plurality of slots (115) laterally aligns with a corresponding staple forming pocket (158) of anvil (150). As best seen in FIG. 8, stapling head assembly (110) presents a plurality of circular recesses (122) within longitudinal channel (118) of stapling head assembly (110). Each circular recess (122) defines a respective top surface (121). Each top surface (121) is oriented at an oblique angle substantially similar to the oblique angle of staple forming pockets (158) and slots (115). A distal portion of each circular recess (122) is in communication with a respective slot (115) via an opening (123). Each circular recess (122) presents an opening (124) that extends from a respective top surface (121) of each circular recess (122) into stapling head assembly (110). Each axle (214) of the plurality of wheel assemblies (210) is rotatably disposed within a respective opening (124) such that each wheel assembly (210) rotates within a respective circular recess (122). Each wheel assembly (210) is oriented within a respective circular recess (122) such that pin (216) extends through a respective opening (123) and into slot (115) of stapling head assembly (110).

Each staple cartridge (230) comprises a drive sled (232), plurality of staples (172), a plate (239), a wave spring (240), and a cartridge body (242). Slots (115) are each configured to selectively receive and temporarily secure a single staple cartridge (230) in stapling head assembly (110). Drive sled (232) comprises a pair of projections (234A, 234B) extending transversely from a base (236) of drive sled (232). Projections (234A, 234B) define a channel (238) between them. Base (236) of drive sled (232) presents a staple engagement surface (237) that is configured to engage and drive staples (172) as will be discussed in more detail below. As best seen in FIGS. 19A-19E, staple engagement surface (237) of the present example has a curved cross-sectional profile, with a radius selected to complement the radius of the crown of each staple (172). Of course, staple engagement surface (237) may have any other suitable configuration.

Cartridge body (242) defines a pair of slots (244) within opposing interior surfaces of at a top of cartridge body (242). Slots (244) are configured to slidably receive base (236) of drive sled (232) such that drive sled (232) freely slides within slots (244) of cartridge body (242). When staple cartridge (230) is assembled, staples (172) are positioned below base (236) of drive sled (232) and above plate (239) within cartridge body (242). Wave spring (240) is disposed below plate (239) and, once staple cartridge (230) is inserted into a respective slot (115), wave spring (240) is configured to resiliently bear against a bottom interior surface of cartridge body (242) and thus exert an upward biasing force upon a bottom surface of plate (239) and staples (172). Cartridge body (242) presents a pair of projections (243) extending inwardly. Projections (243) prevent wave spring (240) from driving drive sled (232) and staples (172) beyond a top surface of cartridge body (242).

Each wheel assembly (210) is further oriented within a respective circular recess (122) such that within each slot (115), a respective pin (216) of each wheel assembly (210) extends into a respective channel (238) of each drive sled (232). Pin (216) is sized such that the diameter of pin (216) is slightly smaller than the width of channel (238) such that pin (216) slides longitudinally within channel (238) freely and such that there is very little gap between an exterior surface of pin (216) and interior surfaces of channel (238). As will be discussed in more detail below, rotation of wheel assembly (210) is configured to cause movement of drive sled (232) relative to cartridge body (242).

Figure 18A:
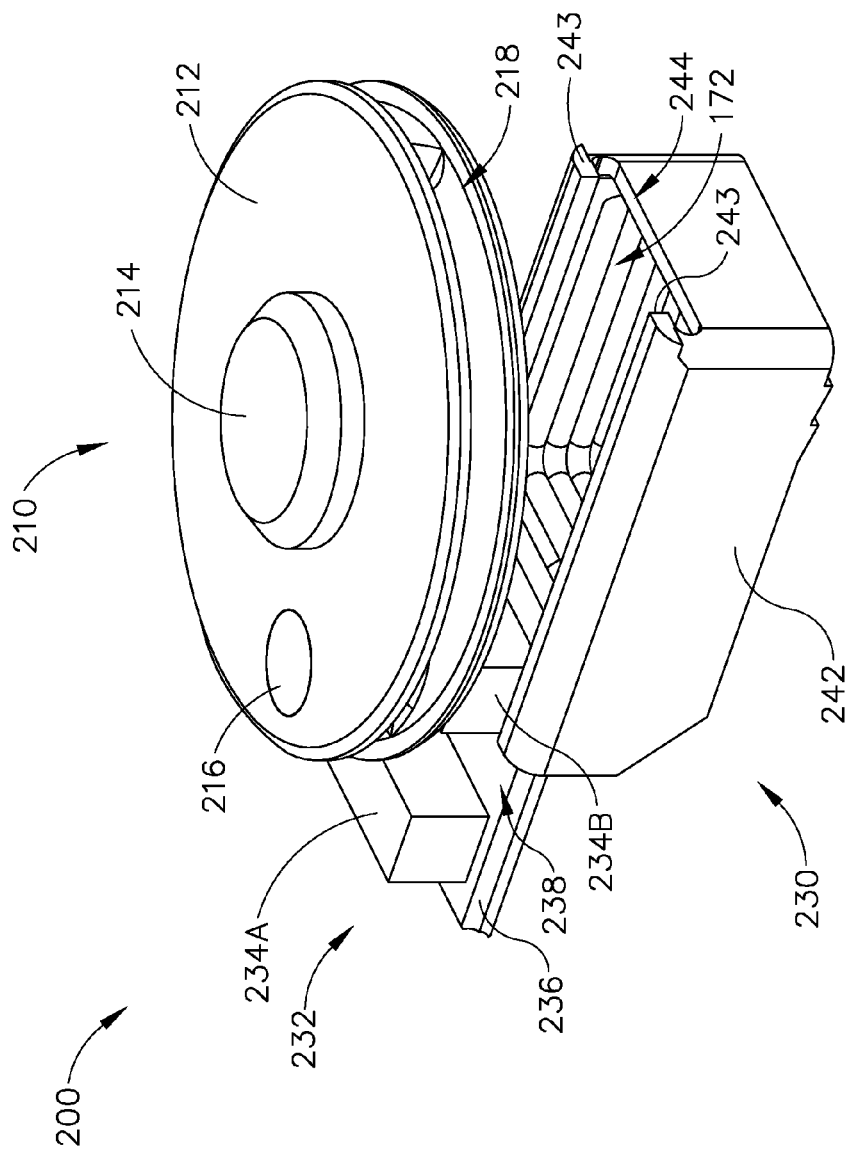
FIG. 18A depicts a perspective view of the stapling assembly of FIG. 16 with a wheel assembly, a driver, and a staple in a first position.
Figure 18B:
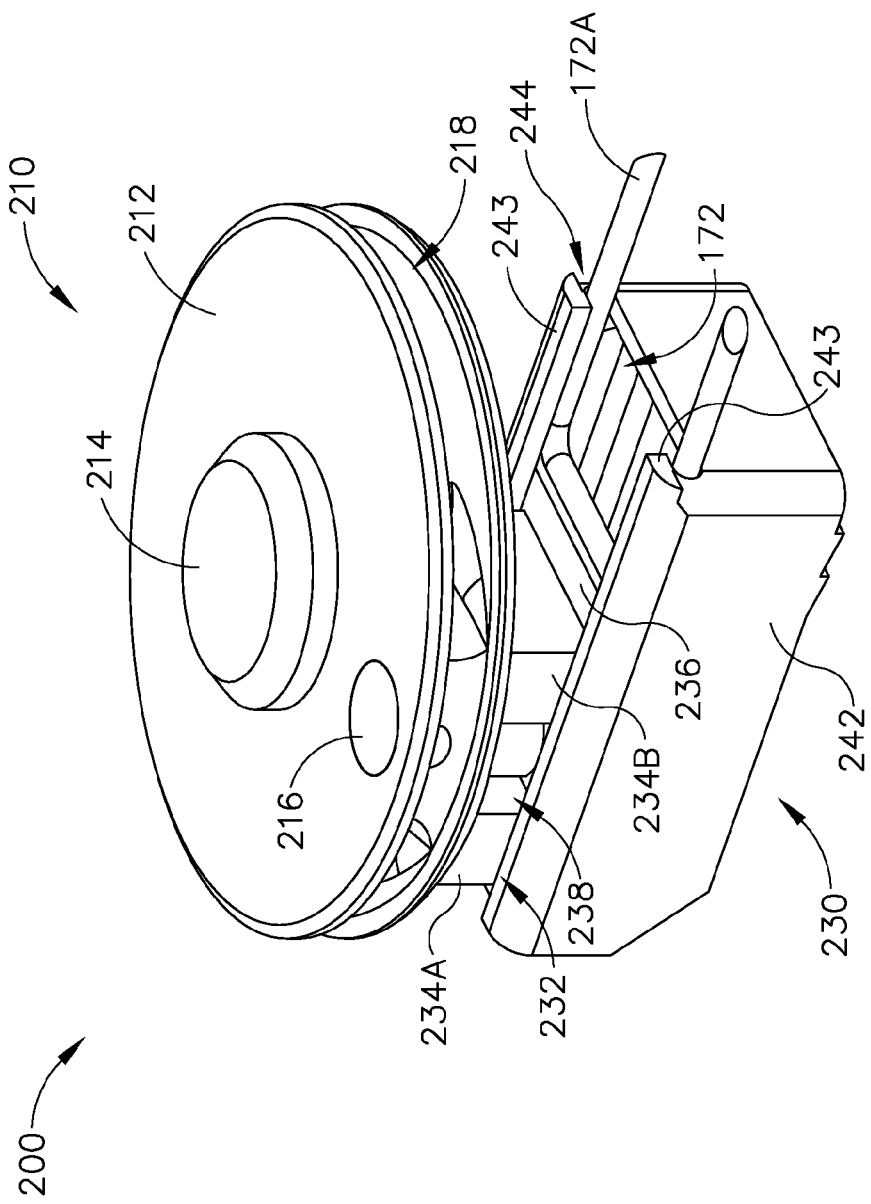
FIG. 18B depicts a perspective view of the stapling assembly of FIG. 16 with the wheel assembly, the driver, and the staple in a second position.
Figure 18C:
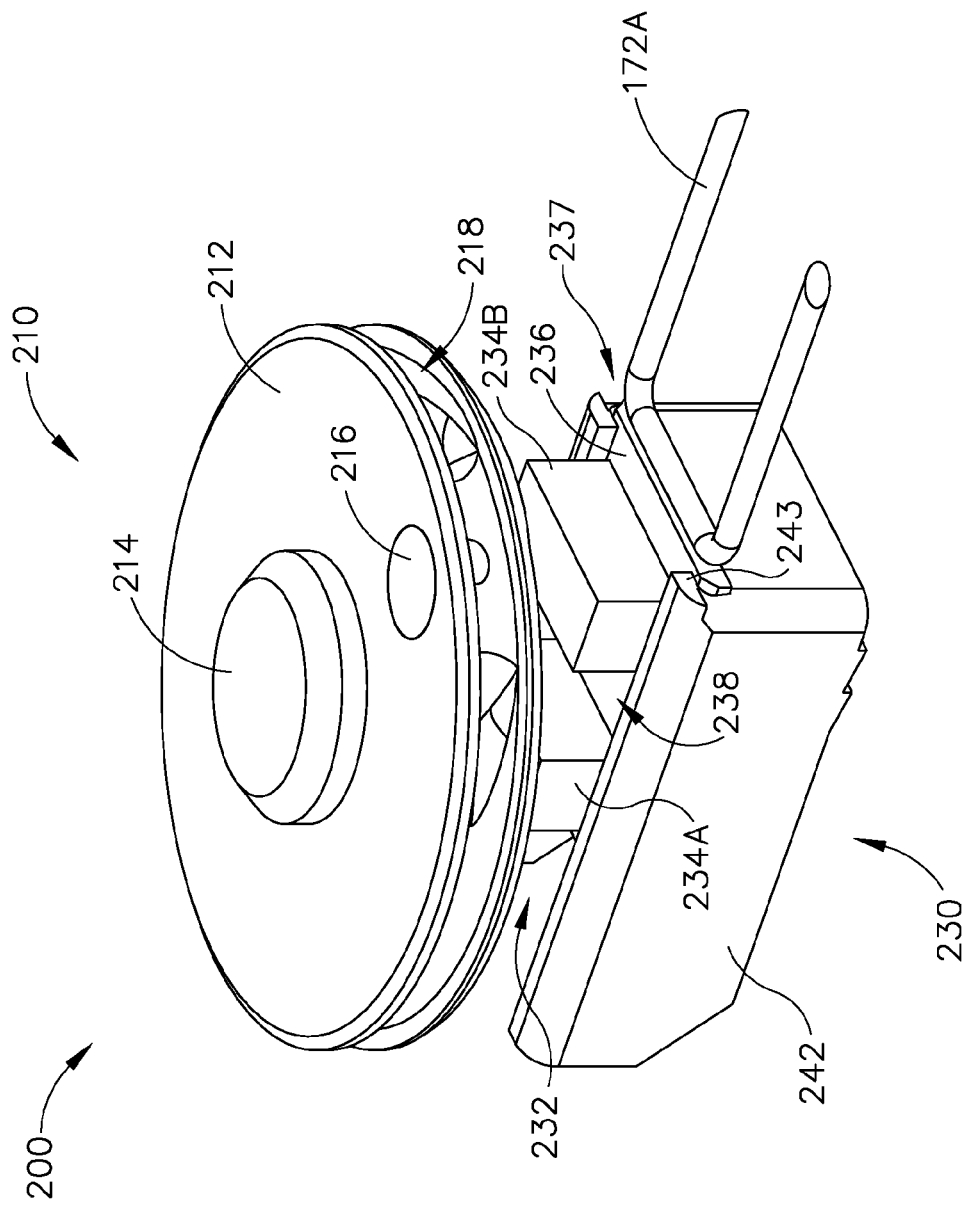
FIG. 18C depicts a perspective view of the stapling assembly of FIG. 16 with the wheel assembly, the driver, and the staple in a third position.
Figure 18D:
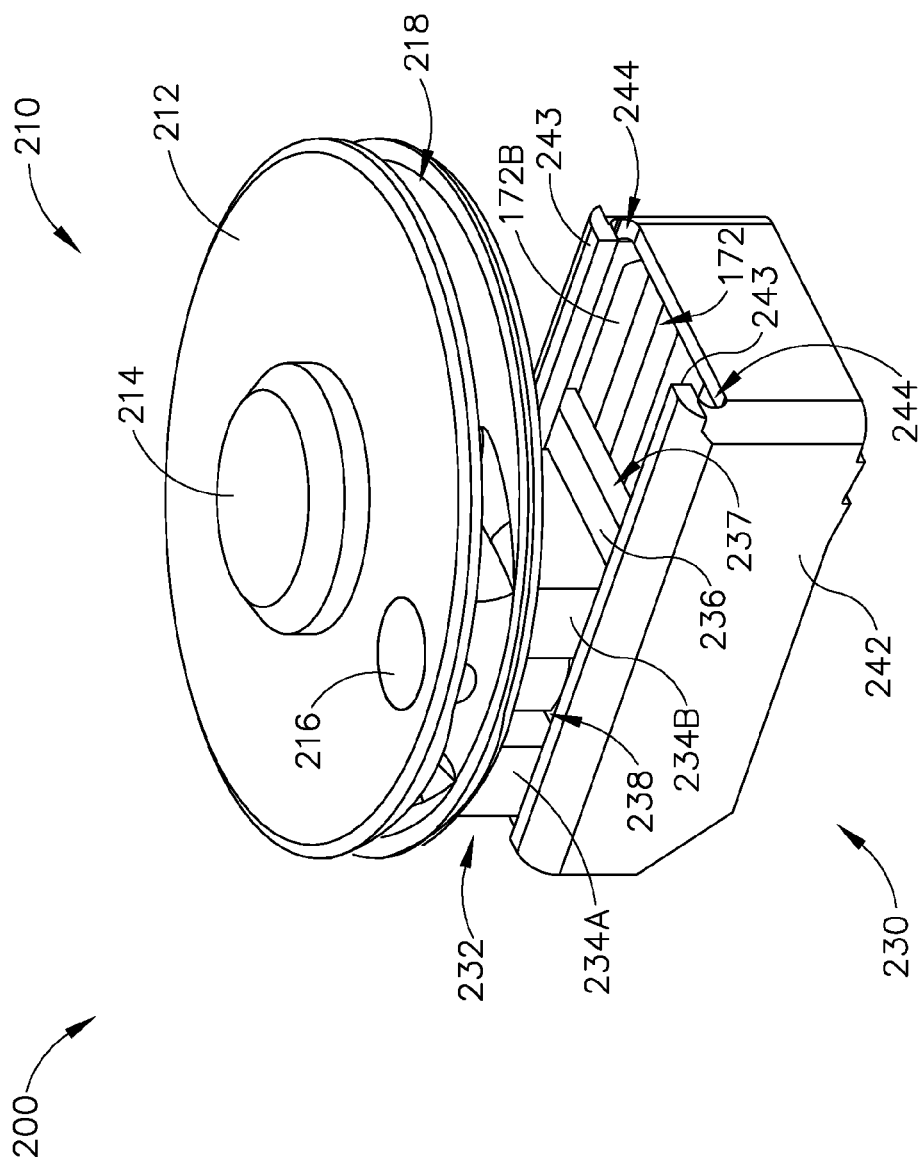
FIG. 18D depicts a perspective view of the stapling assembly of FIG. 16 with the wheel assembly and the driver returned to the second position.
Figure 18E:
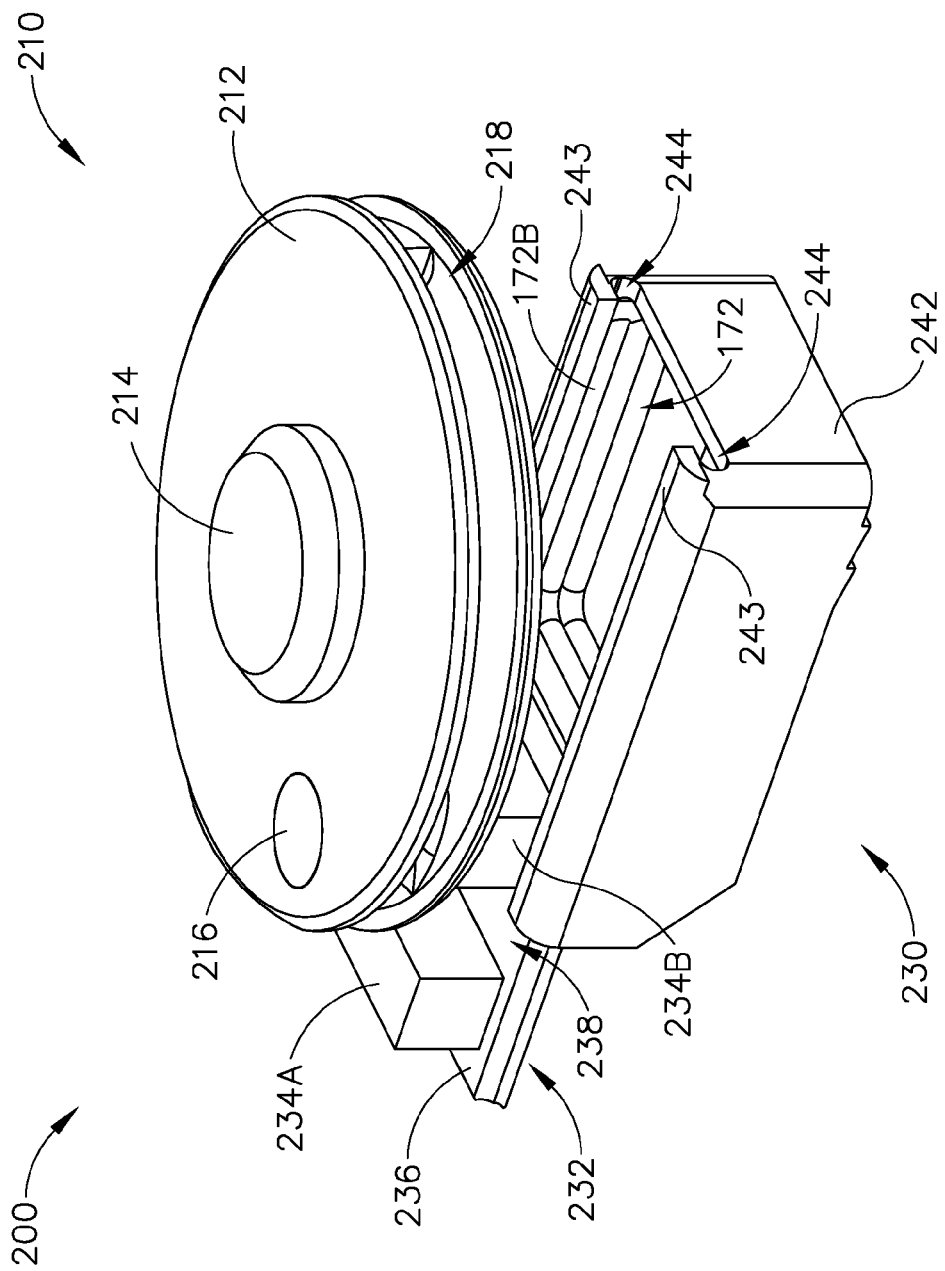
FIG. 18E depicts a perspective view of the stapling assembly of FIG. 16 with the wheel assembly and the driver returned to the first position and with another staple moved into the first position.
Figure 19A:
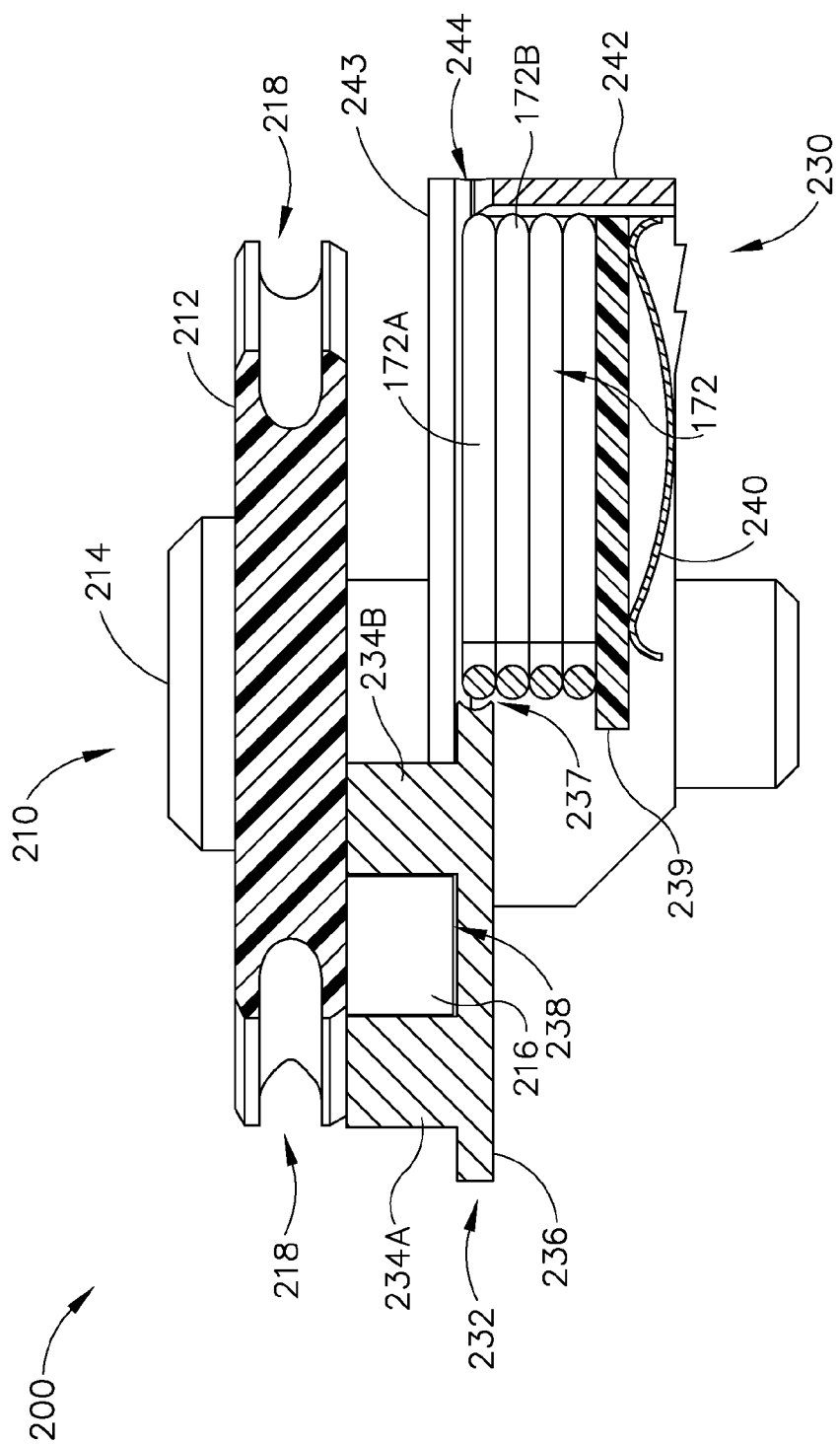
FIG. 19A depicts a cross-sectional view of the stapling assembly of FIG. 16 with the wheel assembly, the driver, and the staple in the first position.

FIGS. 18A-18E and 19A-19E depict the mechanical interaction of wheel assembly (210) and staple cartridge (230). As shown in FIGS. 18A and 19A, with pin (216) of wheel assembly (210) in a first rotational position relative to axle (214), drive sled (232) of stapled cartridge (230) is in a first lateral position. This first lateral position represents a position in which staples (172) are not covered by base (236) of drive sled (232). With drive sled (232) in the first lateral position, wave spring (240) drives staples (172) upwardly relative to cartridge body (242) such that a first staple (172A) of staples (172) is positioned within slots (244), with projections (243) retaining staple (172A) in cartridge body (242). Also, in the first rotational position, pin (216) is in a first longitudinal position relative to channel (238) of drive sled (232). Finally, the first rotational position of wheel assembly (210) correlates with trigger (24) being in the first pivotal position, where trigger (24) is furthest from pistol grip (22).

Figure 19B:
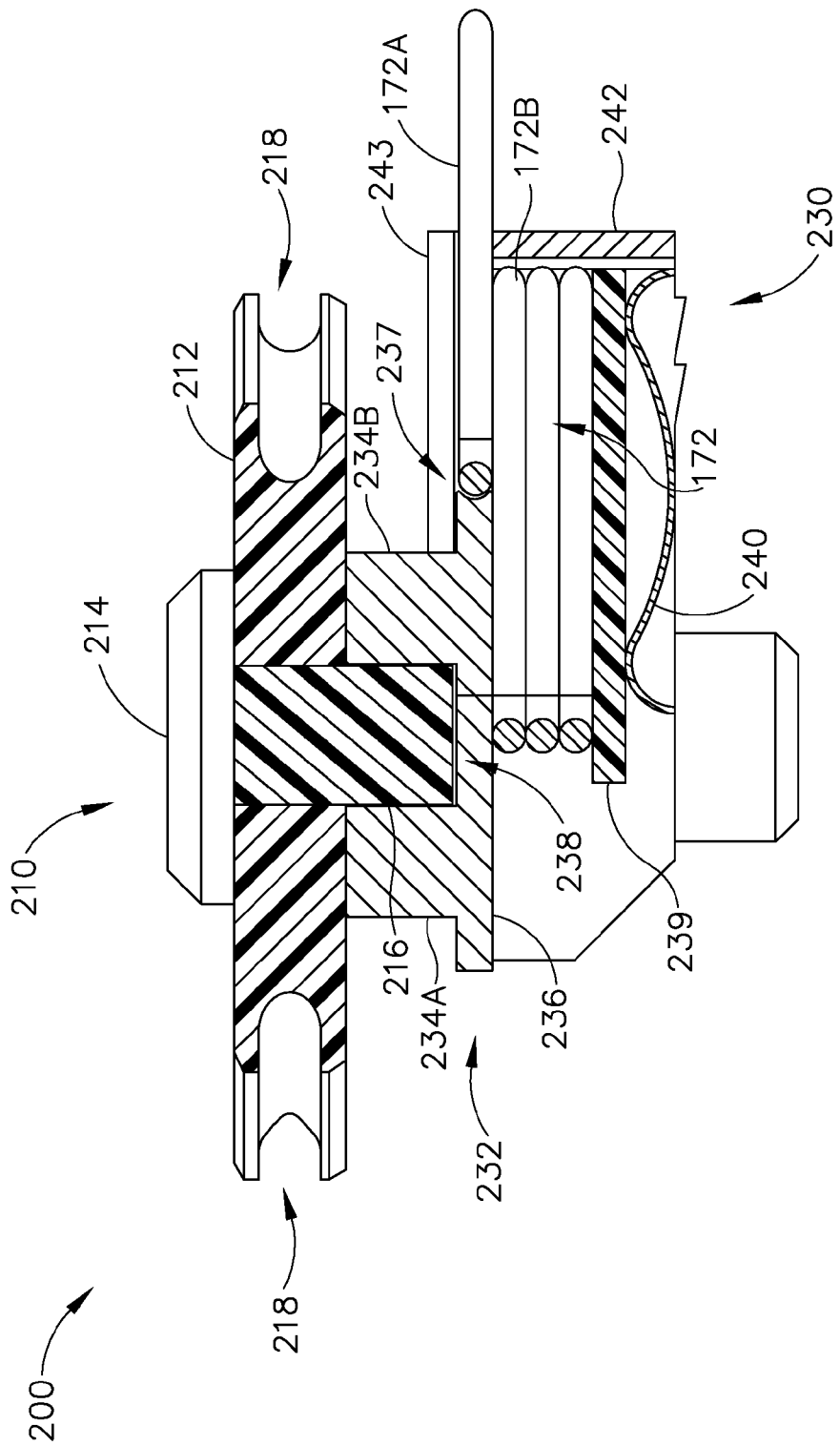
FIG. 19B depicts a cross-sectional view of the stapling assembly of FIG. 16 with the wheel assembly, the driver, and the staple in the second position.

As trigger (24) is pivoted toward pistol grip (22), trigger (24) drives the plurality of cables (32) longitudinally proximally such that wheel assembly (210) is rotated counter-clockwise approximately 90° to a second rotational position as shown in FIGS. 18B and 19B. As pin (216) of wheel assembly (210) is rotated counter-clockwise into the second rotational position, drive sled (232) is transitioned to a second lateral position via contact between the exterior surface of pin (216) and a first interior surface of channel (238) of drive sled (232). As drive sled (232) is transitioned to the second lateral position, staple engagement surface (237) of base (236) engages first staple (172A) and drives first staple (172A) laterally as well. Furthermore, as pin (216) of wheel assembly (210) rotates from the first rotational position to the second rotational position, pin (216) slides longitudinally within channel (238) from the first longitudinal position to a second longitudinal position. It should be understood that the second rotational position of wheel assembly (210) correlates with the second pivotal position of trigger (24), where trigger (24) is approximately midway between the first pivotal position of trigger (24) and pistol grip (22).

Figure 19C:
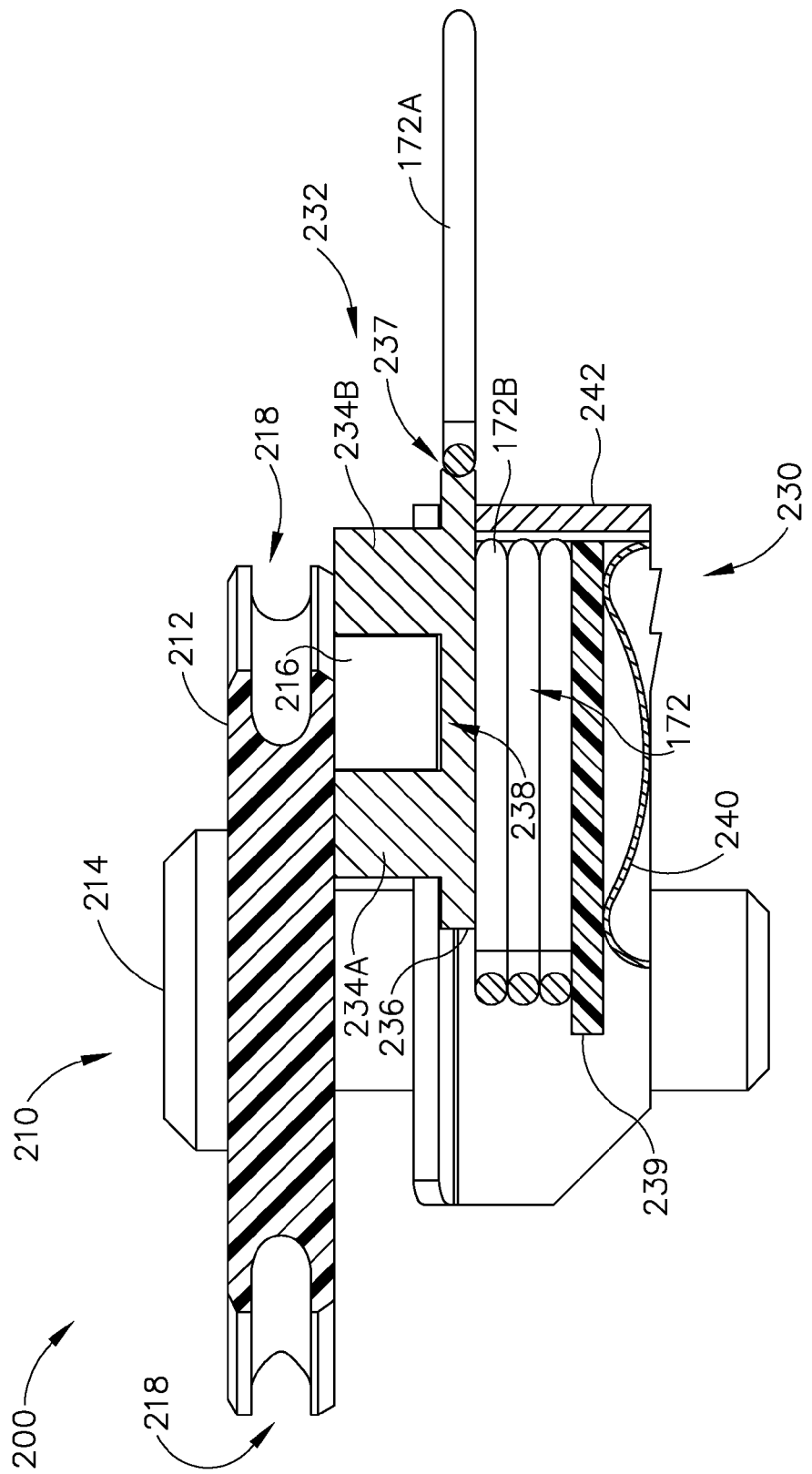
FIG. 19C depicts a cross-sectional view of the stapling assembly of FIG. 16 with the wheel assembly, the driver, and the staple in the third position.

As trigger (24) is pivoted further toward pistol grip (22), trigger (24) further drives the plurality of cables (32) longitudinally proximally such that wheel assembly (210) is further rotated counter-clockwise approximately 90° to a third rotational position as shown in FIGS. 18C and 19C. As pin (216) of wheel assembly (210) is rotated counter-clockwise into the third rotational position, drive sled (232) is transitioned to a third lateral position via contact between the exterior surface of pin (216) and the first interior surface of channel (238) of drive sled (232). As drive sled (232) is transitioned to the third lateral position, drive sled (232) drives first staple (172A) further laterally as well. As will be discussed in more detail below, it is in this lateral position, that first staple (172A) is driven into and formed by a corresponding staple pocket (158) of anvil (150). Furthermore, as pin (216) of wheel assembly (210) rotates from the second rotational position to the third rotational position, pin (216) slides longitudinally within channel (238) from the second longitudinal position back to the first longitudinal position. It should be understood that the third rotational position of wheel assembly (210) correlates with the third pivotal position of trigger (24), where trigger (24) is closest to pistol grip (22).

Figure 19D:
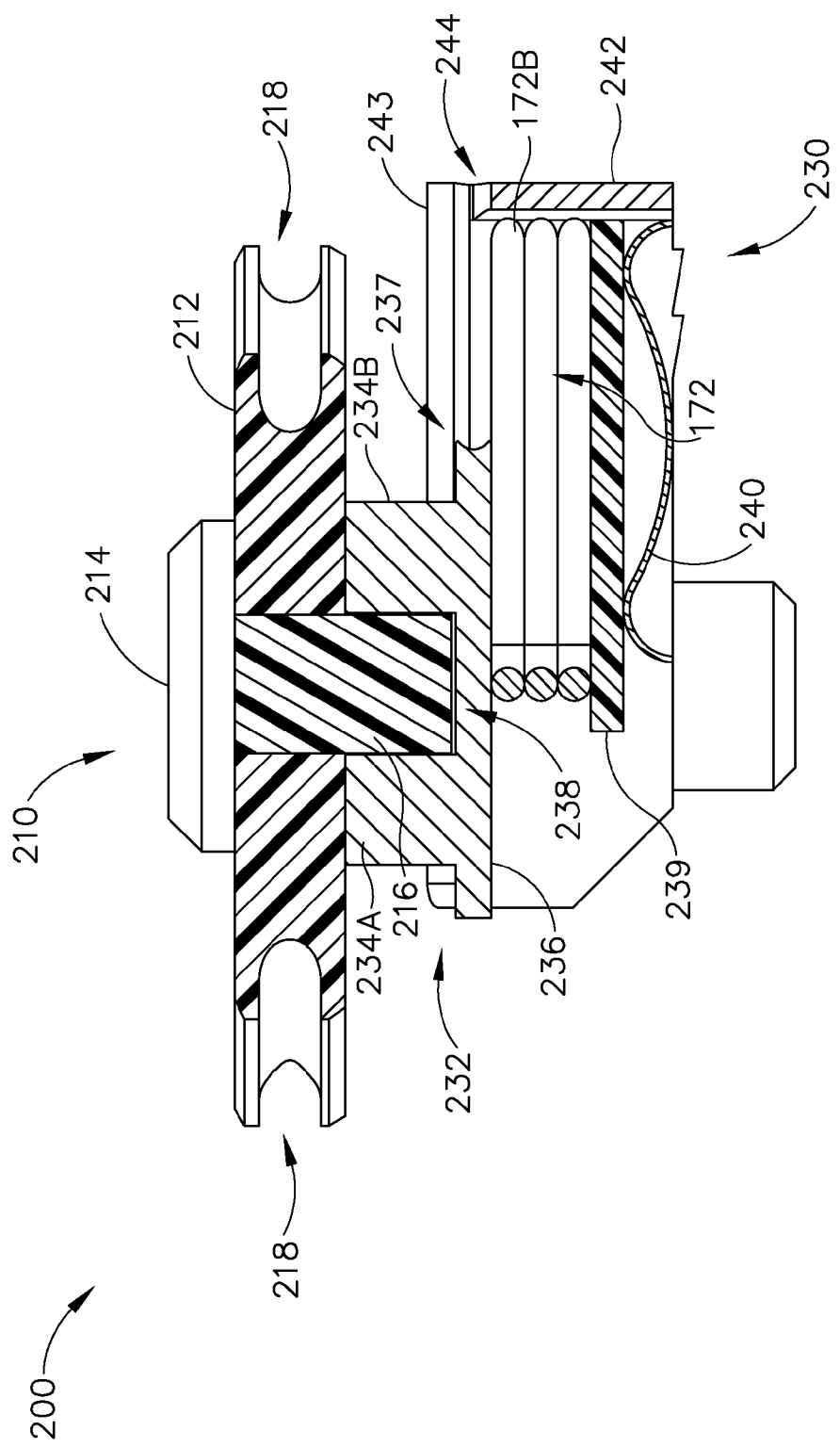
FIG. 19D depicts a cross-sectional view of the stapling assembly of FIG. 16 with the wheel assembly and the driver returned to the second position.

Once trigger (24) is released the distal bias applied to cables (32) drives trigger (24) away from pistol grip (22), and cables (32) are driven longitudinally distally such that wheel assembly (210) is rotated clockwise approximately 90° back to the second rotational position as shown in FIGS. 18D and 19D. As pin (216) of wheel assembly (210) is rotated clockwise back to the second rotational position, drive sled (232) is transitioned back to the second lateral position via contact between the exterior surface of pin (216) and a second interior surface of channel (238) of drive sled (232). Furthermore, as pin (216) of wheel assembly (210) rotates from the third rotational position back to the second rotational position, pin (216) slides longitudinally within channel (238) from the first longitudinal position to the second longitudinal position. Again, the second rotational position of wheel assembly (210) correlates with the second pivotal position of trigger (24), where trigger (24) is approximately midway between the first pivotal position of trigger (24) and pistol grip (22).

Figure 19E:
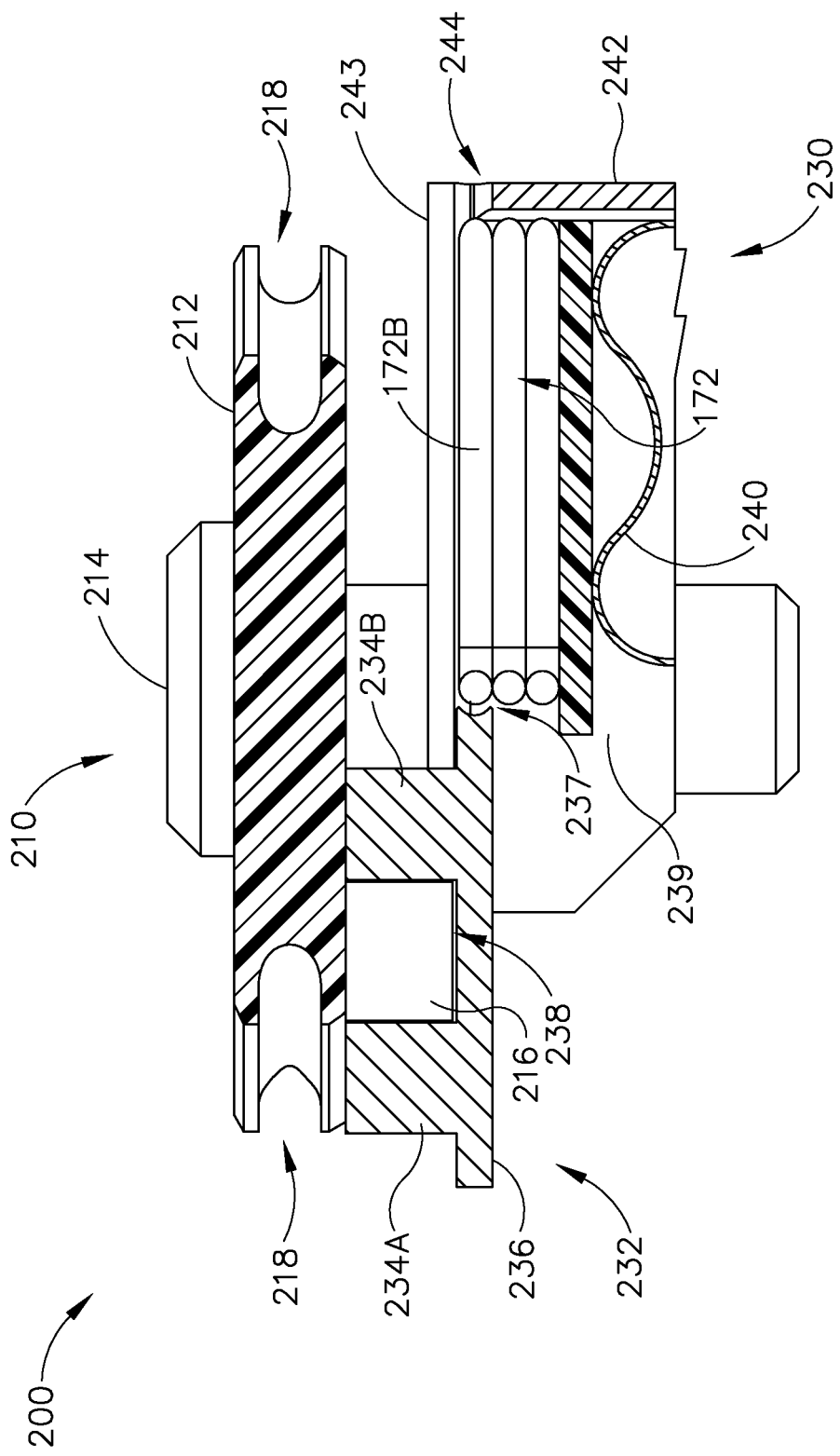
FIG. 19E depicts a cross-sectional view of the stapling assembly of FIG. 16 with the wheel assembly and the driver returned to the first position and with the other staple moved into the first position.

As trigger (24) is further driven away from pistol grip (22) via cables (32), cables (32) are further driven longitudinally distally such that wheel assembly (210) is further rotated clockwise approximately 90° back to the first rotational position as shown in FIGS. 18E and 19E. As pin (216) of wheel assembly (210) is rotated clockwise back to the first rotational position, drive sled (232) is transitioned back to the first lateral position via contact between the exterior surface of pin (216) and the second interior surface of channel (238) of drive sled (232). Again, this first lateral position represents a position in which plurality of staples (172) is not covered by base (236) of drive sled (232). With drive sled (232) in the first lateral position, wave spring (240) drives plurality of staples (172) upwardly relative to cartridge body (242) such that a second staple (172B) of the plurality of staples (172) is positioned within slots (244), with projections (243) retaining staple (172B) in cartridge body (242). Furthermore, as pin (216) of wheel assembly (210) rotates from the second rotational position back to the first rotational position, pin (216) is slid longitudinally within channel (238) from the second longitudinal position back to the first longitudinal position. Again, the first rotational position of wheel assembly (210) correlates with trigger (24) being in the first pivotal position, where trigger (24) is furthest from pistol grip (22).

It should be understood from the foregoing that movement of trigger (24) from the first pivotal position to the third pivotal position and back to the first pivotal position, will drive staples (172) (a single staple (172) from each stapling assembly (200)) laterally such that staples (172) are driven laterally through tissue (2) and into staple forming pockets (158) of anvil (150). It should also be understood that staples (172) may alternatively be driven using a variety of other structures, features, and techniques. By way of example only, while stapling assemblies (200) are all actuated simultaneously in the present example, it should be understood that stapling assemblies (200) may instead be actuated in a sequence. It should also be understood that each stapling assembly (200) may have its own associated cable (32) that runs along the length of shaft assembly (30). In some such versions, stapling assemblies (200) may be actuated independently from each other. In some other versions, a single cable extends along the length of shaft assembly (30) and is then split into separate cables (32), on a per stapling assembly (200) basis, at a coupling located at or near end effector (100). As yet another merely illustrative example, the two distal-most stapling assemblies (200) may be simultaneously driven by a first shared cable (32) while the two proximal-most stapling assemblies (200) are simultaneously driven by a second shared cable (32). As still another merely illustrative example, wheel assemblies (210) may be joined by rigid links (like wheels on a locomotive train), with the proximal-most wheel (212) being the only one directly coupled with a cable (32). It should also be understood that one or more lockout features may be incorporated to prevent stapling assemblies (200) from being actuated before anvil (150) reaches a closed position. Various other suitable alternatives will be apparent to those of ordinary skill in the art in view of the teachings herein.

4. Exemplary Full Sequence of Operation of End Effector

FIGS. 20A-22 depict exemplary stages in a full sequence of operation of end effector (100). It should be understood that cover (112) and vacuum head (130) are omitted from FIGS. 21A-21G for the sake of clarity. The stages shown in FIGS. 20A-22 occur after end effector (100) has been inserted transorally through a patient's esophagus and into the patient's stomach. Articulation section (40) has been actuated to position end effector (100) at an orientation suitable for forming a plication in the tissue (2) of the patient's stomach. For instance, articulation section (40) may be manipulated such that engaging surface (134) of vacuum head (130) is substantially parallel to the mucosal tissue (2) of the patient's stomach. In some instances, end effector (100) may be positioned adjacent to the anterior region of mucosal tissue (2) of the patient's stomach. In some other instances, end effector (100) may be positioned adjacent to the posterior region of mucosal tissue (2) of the patient's stomach. Alternatively, end effector (100) may be positioned adjacent to the region of mucosal tissue (2) associated with the greater curvature or the lesser curvature of the patient's stomach, in the vicinity of the fundus of the patient's stomach or in the vicinity of the antrum of the stomach.

Figure 21A:
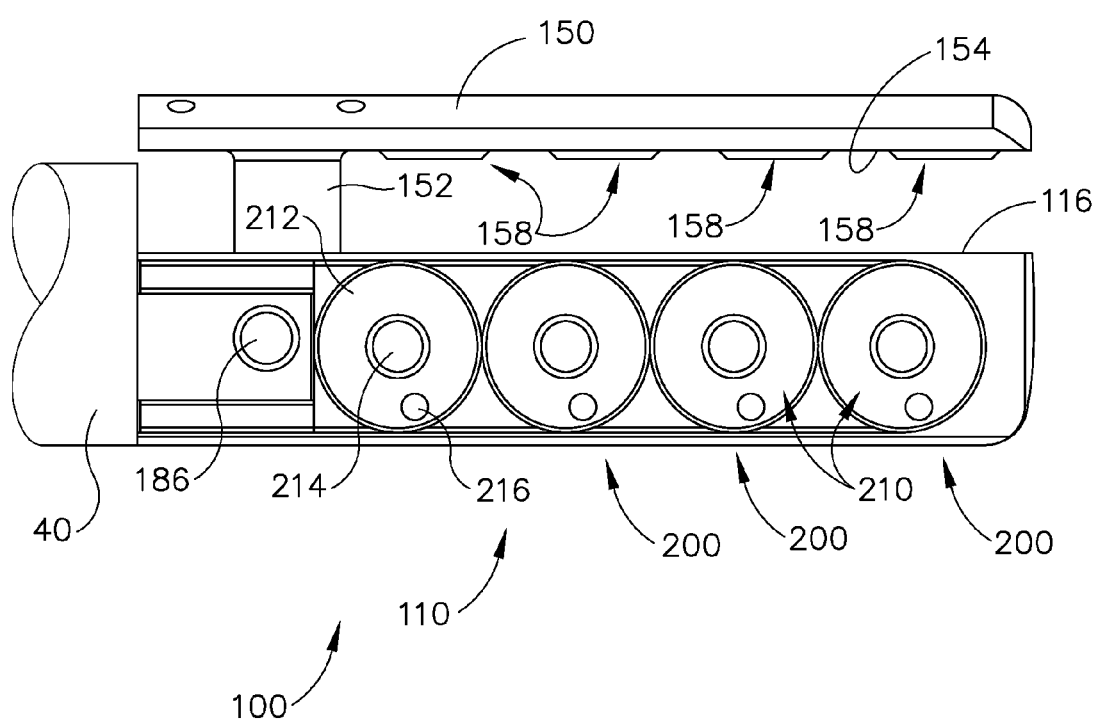
FIG. 21A depicts a top view of the end effector of FIG. 6 with the anvil of FIG. 9 in the first position and with the wheel assemblies of the end effector of FIG. 6 in the first position.
Figure 21B:
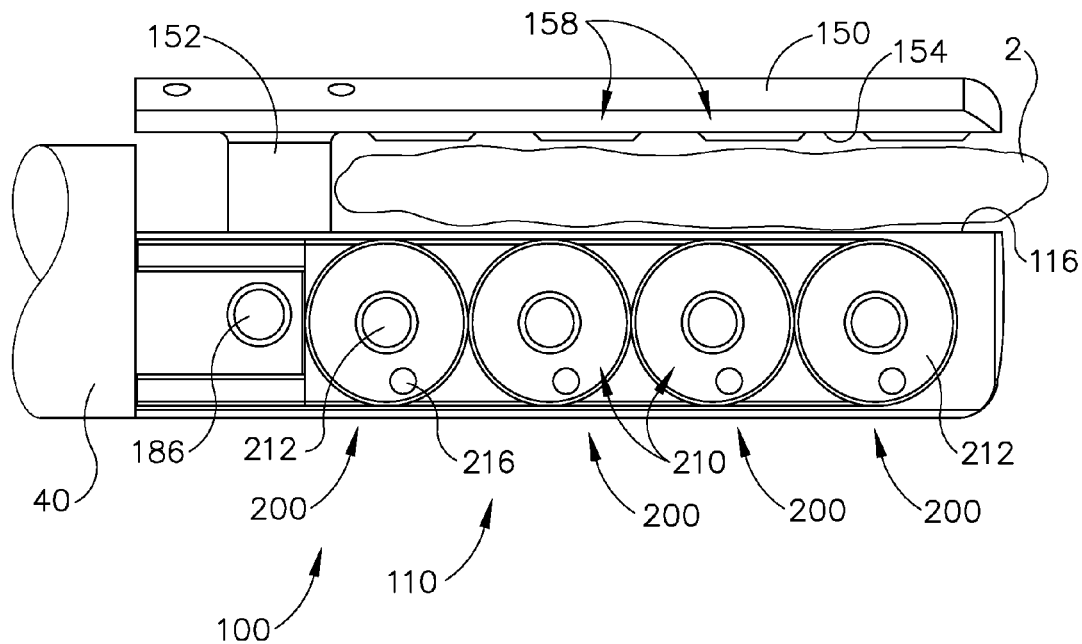
FIG. 21B depicts a top view of the end effector of FIG. 6 with the anvil of FIG. 9 in the first position, with the wheel assemblies of the end effector of FIG. 6 in the first position, and with tissue drawn between the anvil and the staple deck.
Figure 21C:
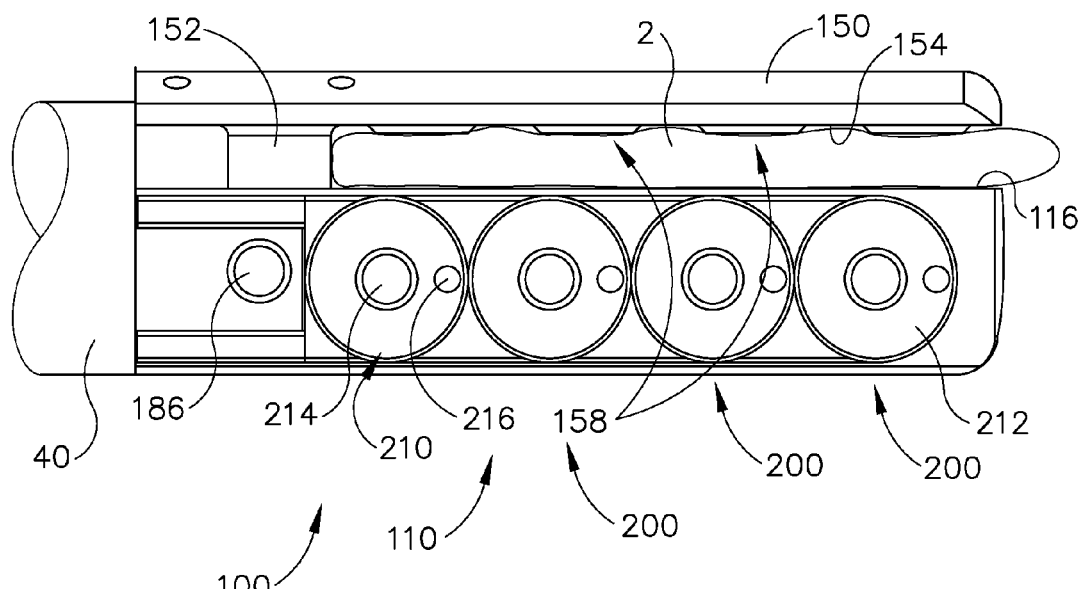
FIG. 21C depicts a top view of the end effector of FIG. 6 with the anvil of FIG. 9 in the second position, beginning to compress the tissue between the anvil and the staple deck, and with the wheel assemblies of the end effector of FIG. 6 in the second position.
Figure 21D:
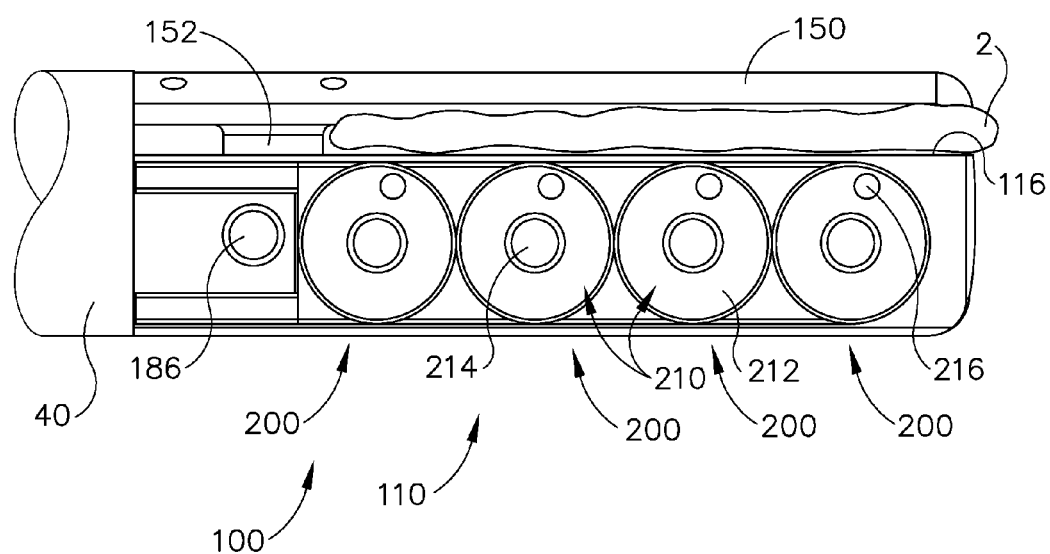
FIG. 21D depicts a top view of the end effector of FIG. 6 with the anvil of FIG. 9 in the third position, fully compressing the tissue between the anvil and the staple deck, and with the wheel assemblies of the end effector of FIG. 6 in the third position.

As shown in FIG. 21A, with anvil (150) in the first lateral position, wheel assemblies (210) are in the first rotational position. In the first lateral position, tissue (2) is gathered between interior surface (154) of anvil (150) and deck (116) of stapling head assembly (110) by vacuum head (130) as shown in FIGS. 20A and 21B. In particular, with vacuum head (130) in the second vertical position, a vacuum source is activated and vacuum head (130) draws tissue (2) against tissue engaging surface (134) of vacuum head (130). As palm trigger (25) is pivoted toward pistol grip (22), cable (36) is drawn proximally to thereby raise vacuum head (130) and drawn tissue (2) from the second position to the third position through the gap between interior surface (154) of anvil (150) and deck (116) of stapling head assembly (110) thereby creating a gastric plication as shown in FIG. 20B.

Tissue (2) is then compressed between interior surface (154) of anvil (150) and deck (116) of stapling head assembly (110) by pivoting trigger (24) toward pistol grip (22) as shown in FIG. 20C-20D and FIGS. 21C-21D. In particular, as trigger (24) is pivoted toward pistol grip (22), anvil (150) is driven laterally from the first lateral position shown in FIGS. 20A-20B and 21A-21B, to the second lateral position shown in FIGS. 20C and 21C, and finally to the third lateral position shown in FIGS. 20D and 21D, to thereby compress tissue (20) between interior surface (154) of anvil (150) and deck (116) of stapling head assembly (110). During this transition, wheel assemblies (210) are rotated from the first rotational position, to the second rotational position, and then to the third rotational position such that at the point where tissue (2) is completely compressed between interior surface (154) of anvil (150) and deck (116) of stapling head assembly (110).

Figure 20E:
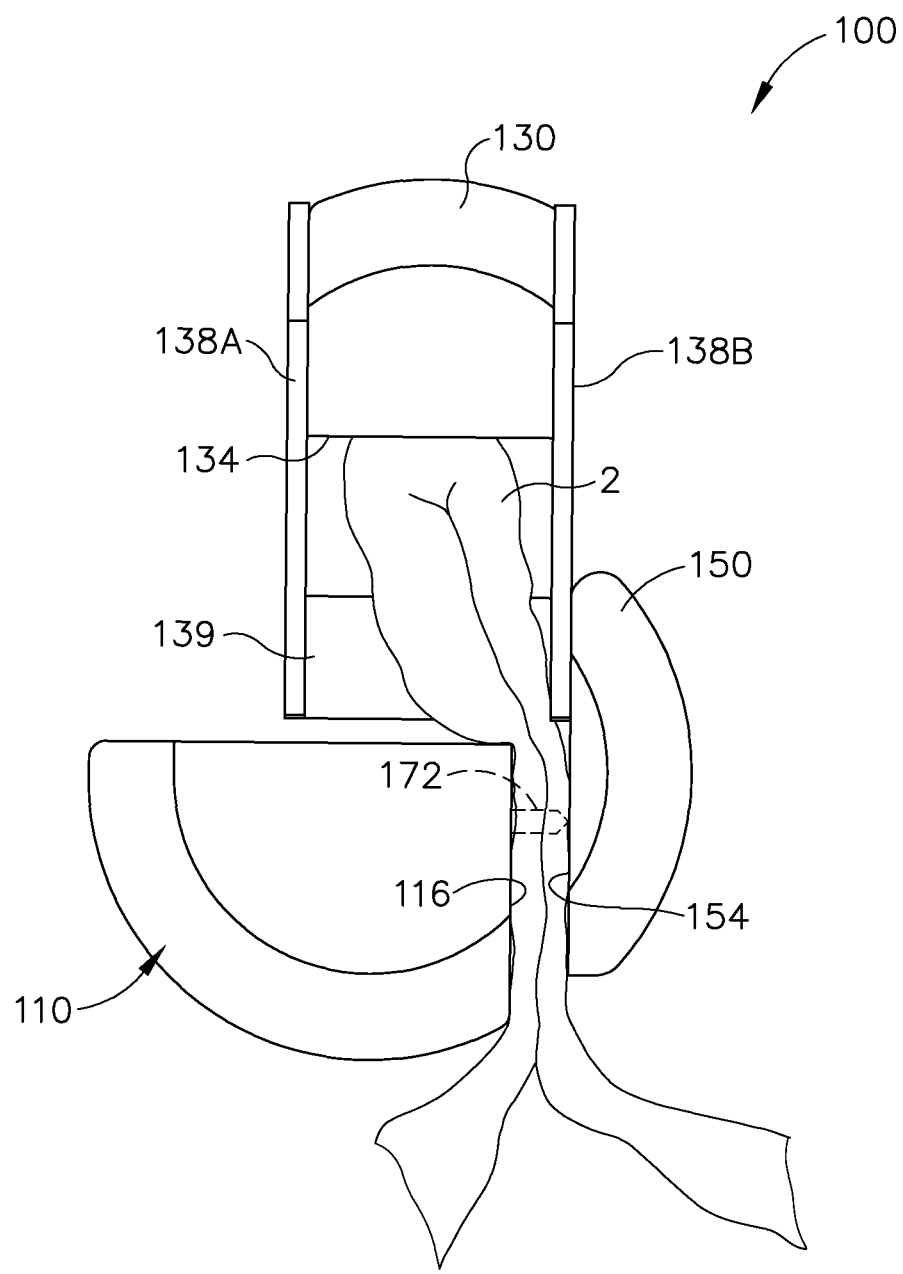
FIG. 20E depicts a front elevational view of the end effector of FIG. 6 with the anvil of FIG. 9 in the third position, with the vacuum port in the third position, and with a plurality of staples being driven through the compressed tissue.
Figure 20F:
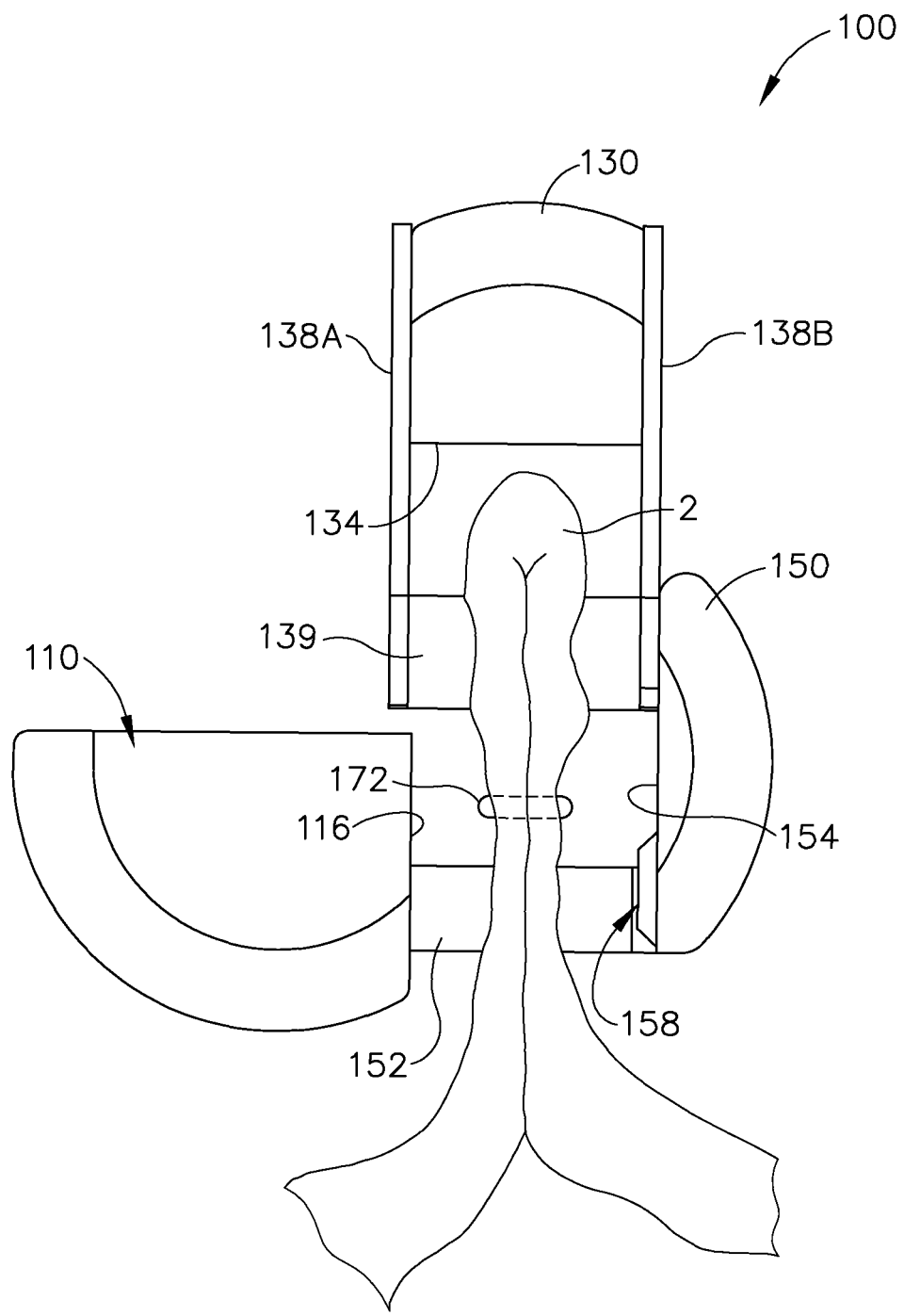
FIG. 20F depicts a front elevational view of the end effector of FIG. 6 with the anvil of FIG. 9 returned to the first position to release the stapled tissue, with the vacuum port in the third position further releasing the stapled tissue, and with the plurality of staples of FIG. 20E driven completely through the tissue.
Figure 21E:
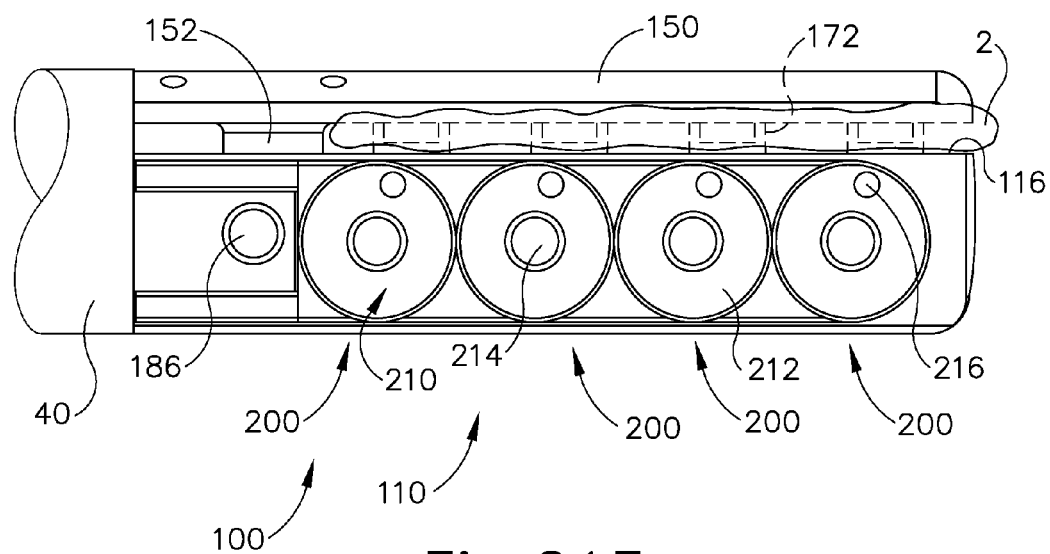
FIG. 21E depicts a top view of the end effector of FIG. 6 with the anvil of FIG. 9 in the third position, with the wheel assemblies of the end effector of FIG. 6 in the third position, and with a plurality of staples being driven through the compressed tissue.

Once tissue (2) is completely compressed between interior surface (154) of anvil (150) and deck (116) of stapling head assembly (110), drive sleds (232) of stapling assemblies (200) are actuated to thereby drive staples (172) (a single staple (172) from each stapling assembly (200)) through tissue (2) as shown in FIGS. 20E and 21E, and into staple forming pockets (158) of anvil (150). It should be understood that cables (32) and/or other features of instrument (10) may be configured to provide full closure of anvil (150) at the position shown in FIGS. 20D and 21D before staples (172) are driven into tissue (2), with anvil (150) movement ceasing while staples (172) are being driven into tissue (2). By way of example only, a clutch mechanism may automatically transfer motion of trigger (24) from anvil (150) to stapling assemblies (200) upon full closure of anvil (150) at the position shown in FIGS. 20D and 21D. As another merely illustrative example, separate triggers may be provided to actuate anvil (150) and stapling assemblies (200). Various suitable ways in which the actuation of anvil (150) and stapling assemblies (200) may be appropriately sequenced will be apparent to those of ordinary skill in the art in view of the teachings herein.

Figure 21F:
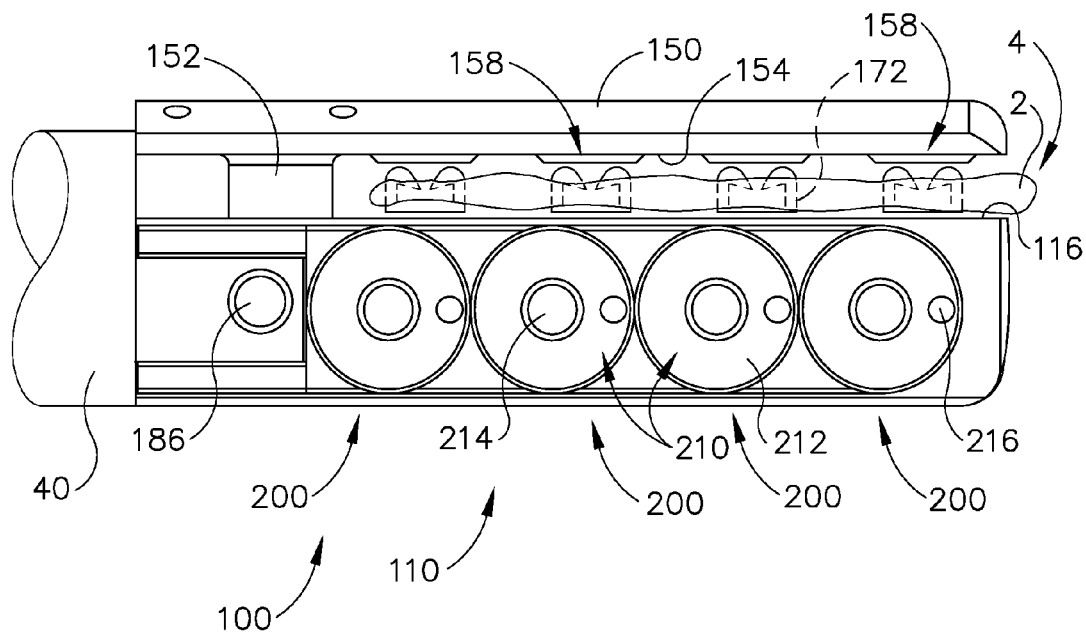
FIG. 21F depicts a top view of the end effector of FIG. 6 with the anvil of FIG. 9 returned to the second position to begin releasing the stapled tissue, with the wheel assemblies of the end effector of FIG. 6 returned to the second position, and with the plurality of staples of FIG. 21E driven completely through the tissue.
Figure 21G:
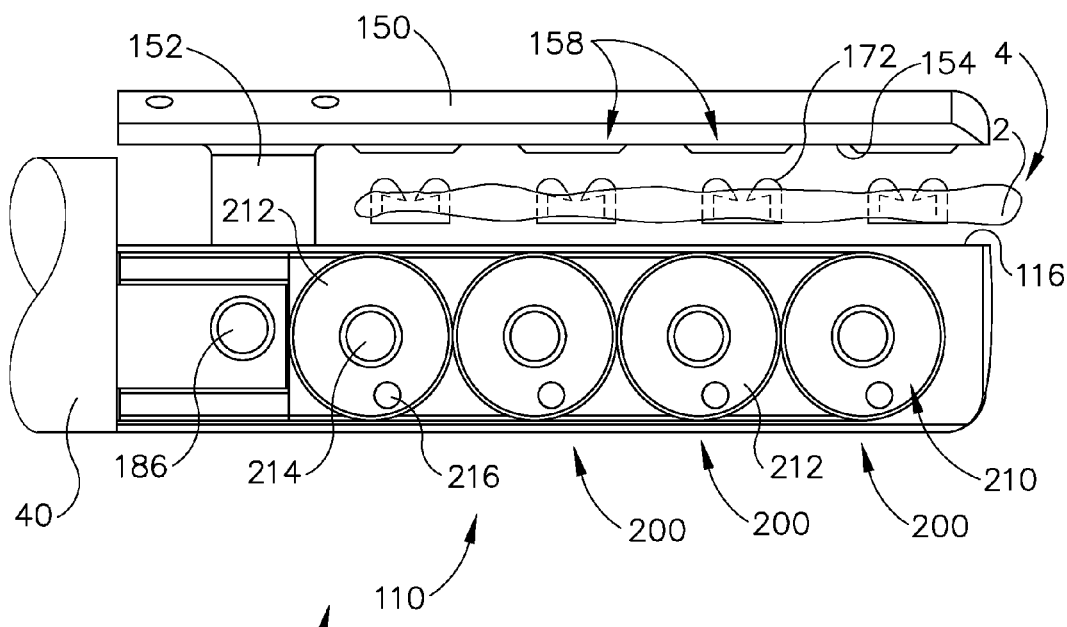
FIG. 21G depicts a top view of the end effector of FIG. 6 with the anvil of FIG. 9 returned to the first position to fully release the stapled tissue, with the wheel assemblies of the end effector of FIG. 6 returned to the first position to index the next set of staples, and with the plurality of staples of FIG. 20E driven completely through the tissue.
Figure 22:
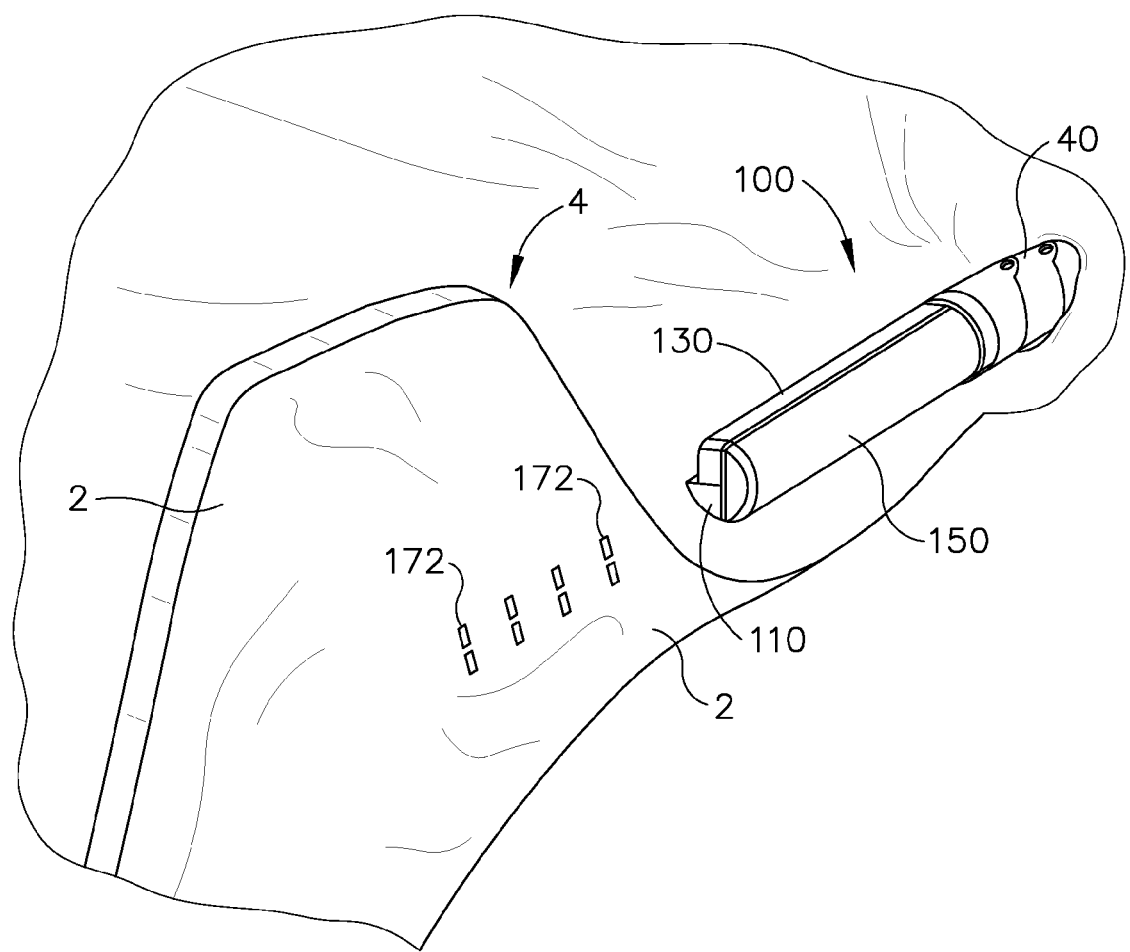
FIG. 22 depicts a perspective view of tissue stapled by the end effector of FIG. 6.

After the plurality of staples have been driven through tissue (2) and formed by staple forming pockets (158), trigger (24) is released to thereby drive anvil (150) from the third lateral position to the first lateral position, and vacuum head (130) releases the tissue by stopping suction, leaving behind a stapled plication (4) as shown in FIGS. 21F-21G and 22. In some instances, suction is stopped at vacuum head (130) once tissue (2) is sufficiently compressed between anvil (150) and deck (116) of stapling head assembly (110). In some other instances, suction is not stopped at vacuum head (130) until staples (172) are fully deployed in tissue (2) and formed by anvil (150).

Plication (4) reduces the capacity of the stomach in this example. It should be understood that the plication (4) may include all layers of stomach tissue, such that plication (4) provides apposed regions of serosa on the exterior of the patient's stomach. It should be further understood that, over time, such apposition of serosa may ultimately result in serosa-to-serosa bonding. In some such instances, the serosa-to-serosa bond may maintain the plication even if staples (172) eventually biodegrade or are absorbed.

In some instances, it may be desirable to apply several series of staples (172) to tissue (2). For instance, it may be desirable to apply several series of staples (172) to a single plication (4) of tissue (2), such as to further secure the plication (4) or to increase the size of the plication (4). A second row of staples (172) may be applied in line with the first row of staples (172), offset from the first row of staples (172), or otherwise. As another merely illustrative example, it may be desirable to create several plications (4) within the stomach, such as one or more plications (4) at the anterior side of the stomach in combination with one or more plications (4) at the posterior side of the stomach. As noted above, each stapling assembly (200) is preloaded with four staples (172). It should therefore be understood that end effector (100) may be actuated four times to apply four series of staples (172). Of course, any other suitable number of staples (172) may be preloaded into each stapling assembly (200).

There are numerous other ways in which more than series of staples (172) may be applied to tissue (2) within a single procedure. By way of example only, several instruments (10) may be used, each instrument (10) being actuated to create a corresponding single plication (4) (or four corresponding sets of staple rows). As another merely illustrative example, end effector (100) may be configured to enable replacement of staple cartridges (230). Alternatively, end effector (100) may enable replacement of stapling head assembly (110). Alternatively, instrument (10) may enable replacement of end effector (100). Various suitable ways in which instrument (10) may provide replaceability of one or more components will be apparent to those of ordinary skill in the art in view of the teachings herein. Similarly, various other suitable ways in which instrument (10) may be used will be apparent to those of ordinary skill in the art in view of the teachings herein.

III. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a shaft assembly extending distally from the body, wherein the shaft assembly comprises a proximal end and a distal end; and
   (c) an end effector coupled with the distal end of the shaft assembly, wherein the end effector comprises:
      (i) a stapling head assembly, wherein the stapling head assembly comprises a first staple, a second staple, a first rotary member, and a second rotary member, wherein the first rotary member is rotatable about a first axis, wherein the second rotary member is rotatable about a second axis, (ii) an anvil, wherein the first rotary member is rotatable about the first axis to drive the first staple toward the anvil, wherein the second rotary member is rotatable about the second axis to drive the second staple toward the anvil, wherein the anvil is operable to form the first and second staples received thereagainst, and (iii) a vacuum head, wherein the vacuum head is operable to draw tissue between the stapling head assembly and the anvil.

2. The surgical instrument of claim 1, wherein the stapling head assembly further comprises a third rotary member, wherein the third rotary member is rotatable about a third axis, and wherein rotating the third rotary member about the third axis is configured to drive the third staple toward the anvil.

3. The surgical instrument of claim 1, wherein the stapling head assembly defines a length along a longitudinal axis, wherein the first and second staples are longitudinally spaced apart from each other along at least part of the length of the stapling head assembly.

4. The surgical instrument of claim 3, wherein the first and second rotary members are operable to drive the staples simultaneously.

5. The surgical instrument of claim 1, wherein the first staple is one of a plurality of first staples, wherein the plurality of first staples are stacked adjacent to each other, wherein the first rotary member is operable to drive each staple of the plurality of first staples in a succession.

6. The surgical instrument of claim 1, wherein at least one of the first and second staples is oriented obliquely relative to a longitudinal axis defined by the stapling head assembly.

7. The surgical instrument of claim 1, further comprising a third rotary member, wherein the third rotary member is operable to drive the anvil toward and away from the stapling head assembly.

8. The surgical instrument of claim 7, wherein the third rotary member is rotatable about a third axis, wherein the third rotary member comprises a pin offset from the third axis, wherein the anvil defines a channel, wherein the pin of the second rotary member is disposed in the channel of the anvil.

9. The surgical instrument of claim 1, wherein the first rotary member comprises a wheel assembly.

10. The surgical instrument of claim 9, wherein the wheel assembly comprises a wheel, a central axle, and an offset pin.

11. The surgical instrument of claim 1, wherein the end effector further comprises a staple cartridge, wherein the first staple is positioned in the staple cartridge.

12. The surgical instrument of claim 11, wherein the staple cartridge comprises a drive sled, wherein the first rotary member is operable to rotate to thereby drive the drive sled from a first position to a second position and back to the first position along a path transverse to a longitudinal axis defined by the stapling head assembly.

13. The surgical instrument of claim 12, wherein the first staple is one of a plurality of first staples, wherein the staple cartridge further comprises the plurality of first staples, wherein the drive sled is operable to drive the plurality of first staples in succession.

14. The surgical instrument of claim 13, wherein the staple cartridge further comprises a resilient member configured to bias the plurality of staples toward the drive sled.

15. The surgical instrument of claim 1, wherein the anvil is movable between a first position and a second position, wherein the anvil is spaced apart from the stapling head assembly in the first position, wherein the anvil is closed against the stapling head assembly in the second position, wherein the end effector is configured to maintain a parallel relationship between the anvil and the stapling head assembly during movement of the anvil from the first position to the second position.

16. The surgical instrument of claim 1, wherein the body comprises a handle assembly having at least one trigger, wherein the shaft includes one or more drive cables, wherein the at least one trigger is operable to actuate the end effector via the one or more drive cables.

17. The surgical instrument of claim 1, wherein the end effector is sized and configured to be passed through a patient's mouth and esophagus, wherein the shaft assembly is sized and configured to position the end effector in the patient's stomach.

18. A surgical instrument comprising:
(a) a body;
(b) a shaft assembly extending distally from the body, wherein the shaft assembly comprises a proximal end and a distal end; and
(c) an end effector coupled with the distal end of the shaft assembly, wherein the end effector comprises:
  (i) a stapling head assembly comprising a plurality of wheel assemblies,
  (ii) an anvil, wherein the anvil is operable form staples driven by the stapling head assembly, wherein a first wheel assembly of the plurality of wheel assemblies is operable to rotate to thereby drive the anvil toward and away from the stapling head assembly, and
  (iv) a staple cartridge, wherein the staple cartridge comprises a plurality of staples, wherein at a second wheel assembly of the plurality of wheel assemblies is operable to rotate to thereby drive at least one staple of the plurality of staples through tissue and toward the anvil.

19. A surgical instrument comprising:
(a) a body;
(b) a shaft assembly extending distally from the body, wherein the shaft assembly comprises a proximal end and a distal end; and
(c) an end effector coupled with the distal end of the shaft assembly, wherein the end effector comprises:
  (i) a stapling head assembly comprising:
    (A) a rotary drive assembly having a rotary member configured to rotate about an axis,
    (B) a first staple, wherein the first staple is positioned to engage the rotary drive assembly, wherein rotary drive assembly is operable to eject the first staple from the stapling head assembly,
    (C) a biasing element, and
    (D) a second staple, wherein the biasing element is configured to resiliently bias the second staple toward the rotary member to engage the rotary drive assembly after ejection of the first staple from the stapling head assembly, and
  (ii) an anvil, wherein the anvil is operable to form staples ejected by the rotary drive assembly,
wherein the rotary member comprises a wheel assembly including a wheel rotatably mounted about the axis and an offset pin, wherein the offset pin extends from the wheel such that the offset pin orbits about the axis as the wheel rotates, and wherein the offset pin is operable to eject the first staple from the stapling head assembly.

* * * * *